United States Patent
Grant et al.

(10) Patent No.: US 11,547,337 B2
(45) Date of Patent: Jan. 10, 2023

(54) SENSOR CONFIGURATION IN MAGNETOMETER FOR MEDICAL USE

(71) Applicant: CREAVO MEDICAL TECHNOLOGIES LIMITED, Leeds (GB)

(72) Inventors: Richard Theodore Grant, Leeds (GB); Benjamin Thomas Hornsby Varcoe, Leeds (GB); Shima Ghasemi Roudsari, Leeds (GB); David Ian Watson, Leeds (GB); Michal Smalera, Leeds (GB)

(*) Notice: Subject to any disclaimer, the term of this patent is extended or adjusted under 35 U.S.C. 154(b) by 659 days.

(21) Appl. No.: 16/492,150

(22) PCT Filed: Nov. 11, 2018

(86) PCT No.: PCT/GB2018/053451
§ 371 (c)(1),
(2) Date: Sep. 8, 2019

(87) PCT Pub. No.: WO2019/106365
PCT Pub. Date: Jun. 6, 2019

(65) Prior Publication Data
US 2020/0077909 A1      Mar. 12, 2020

(30) Foreign Application Priority Data
Nov. 29, 2017    (GB) .................................. 1719876

(51) Int. Cl.
*A61B 5/242*    (2021.01)
*A61B 5/243*    (2021.01)
*A61B 5/245*    (2021.01)

(52) U.S. Cl.
CPC .............. *A61B 5/242* (2021.01); *A61B 5/243* (2021.01); *A61B 5/245* (2021.01); *A61B 2562/0223* (2013.01); *A61B 2562/046* (2013.01)

(58) Field of Classification Search
CPC ......... A61B 5/242; A61B 5/243; A61B 5/245; A61B 5/7203; A61B 2562/0223;
(Continued)

(56) References Cited

U.S. PATENT DOCUMENTS

| | | | |
|---|---|---|---|
| 2014/0077796 A1* | 3/2014 | Schatz | G01R 33/02 324/244 |
| 2015/0150475 A1* | 6/2015 | Varcoe | A61B 5/243 600/409 |

FOREIGN PATENT DOCUMENTS

| | | |
|---|---|---|
| CN | 104427931 A | 3/2015 |
| CN | 105308472 | 2/2016 |

(Continued)

OTHER PUBLICATIONS

Prance, R. J., T. D. Clark, and H. Prance. "Compact broadband gradiometric induction magnetometer system." Sensors and Actuators A: Physical 76.1-3 (1999): 117-121. (Year: 1999).*

(Continued)

*Primary Examiner* — Sean D Mattson
(74) *Attorney, Agent, or Firm* — Vierra Magen Marcus LLP

(57) ABSTRACT

A magnetometer system for medical use comprises one or more induction coils for detecting a time varying magnetic field. Each coil has a maximum outer diameter of 10 cm or less, and a configuration such that the ratio of the coil's length to its outer diameter is 0.9 or more, and the ratio of the coil's inner diameter to its outer diameter is 0.6 or more. Each induction coil comprises a magnetic core. The magnetometer system further comprises a detection circuit (Continued)

coupled to each coil and configured to convert a current or voltage generated in the coil by a time varying magnetic field to an output signal for use to analyse the time varying magnetic field.

19 Claims, 10 Drawing Sheets

(58) Field of Classification Search
CPC .......... A61B 2562/046; G01R 33/0094; G01R 33/0005; G01R 33/02
See application file for complete search history.

(56) References Cited

FOREIGN PATENT DOCUMENTS

| | | | |
|---|---|---|---|
| GB | 2519257 | 4/2015 | |
| JP | 2006296829 | 11/2006 | |
| JP | 2008-154922 | 7/2008 | |
| JP | 2011107126 | 6/2011 | |
| JP | 2015-525596 | 9/2015 | |
| WO | 2014006387 | 1/2014 | |
| WO | WO2014006387 A1 | 1/2014 | |
| WO | 2017109484 | 6/2017 | |
| WO | WO-2017109484 A1 * | 6/2017 | ............... A61B 5/05 |
| WO | WO2017109484 A1 | 6/2017 | |
| WO | 2017/187160 | 11/2017 | |

OTHER PUBLICATIONS

Pellicer-Guridi, Ruben, et al. "Towards ultimate low frequency air-core magnetometer sensitivity." Scientific reports 7.1 (2017): 1-12. (Year: 2017).*
Chinese Office Action dated Sep. 26, 2021, Chinese Patent Application No. 201880031956.4.
GB Combined Search and Examination Report dated Jun. 4, 2019, GB Patent Application No. GB1819446.4.
Japanese Search Report dated Sep. 9, 2020, Japanese Patent Application No. 2019-548308.
PCT International Search Report dated Jan. 21, 2019, PCT Patent Application No. PCT/GB2018/053451.
PCT Written Opinion of the International Searching Authority dated Jan. 21, 2019, PCT Patent Application No. PCT/GB2018/053451.
J. Prance et al., "Compact broadband gradiometric induction magnetometer system", Sensors and Actuators A: Physical, vol. 76, No. 1-3, Aug. 1, 1999 (Aug. 1, 1999), p. 117-121, XP055544665 DOI: 10.1016/S0924-4247(98)00363-X external link.
Prance R J et al, "Compact room-temperature induction magnetometer with superconducting quantum interference device level field sensitivity", Review of Scientific Instruments, AIP, Melville, NY, US, vol. 74, No. 8, Aug. 1, 2003 (Aug. 1, 2003), p. 3735-3739, XP012040989 DOI: 10.1063/1.1590745 external link.

* cited by examiner

SENSOR CONFIGURATION IN MAGNETOMETER FOR MEDICAL USE

The technology described herein relates to methods and apparatus for medical magnetometry, and in particular to methods and apparatus for processing a signal from a magnetometer for medical use, such as for use as a cardiac magnetometer.

It can be useful in many medical situations to be able to measure magnetic fields relating to or produced by the human body for diagnostic purposes. For example, the heart's magnetic field contains information that is not contained in an ECG (Electro-cardiogram), and so a magneto cardiogram scan can provide different and additional diagnostic information to a conventional ECG.

Most modern cardiac magnetometers are built using ultra-sensitive SQUID (Superconducting Quantum Interference Device) sensors. However, SQUID magnetometers are very expensive to operate as they require cryogenic cooling. Their associated apparatus and vacuum chambers are also bulky pieces of equipment. This limits the suitability of SQUID magnetometers for use in a medical environment, for example because of cost and portability considerations.

Another known form of magnetometer is an induction coil magnetometer. Induction coil magnetometers have the advantage over SQUID magnetometers that cryogenic cooling is not necessarily required, they are relatively inexpensive and easy to manufacture, they can be put to a wide range of applications and they have no DC sensitivity.

However, induction coil magnetometers have not been widely adopted for magneto cardiography because magneto cardiography requires low field (<nT), low frequency (<100 Hz) sensing, and common induction coil magnetometer designs that can achieve such sensitivities are too large to be practical for use as a cardiac probe.

The Applicants have addressed these problems in their earlier application WO2014/006387, which discloses a method and apparatus for detecting and analysing medically useful magnetic fields that uses an induction coil or coils of a specific configuration to detect the magnetic field of a subject.

Notwithstanding this, the Applicants believe that there remains scope for alternative arrangements and improvements to the design and use of magnetometers for medical use, and in particular for cardio magnetic sensing and/or imaging.

According to a first aspect of the technology described herein there is provided a magnetometer system for medical use, comprising:

one or more induction coils for detecting a time varying magnetic field, each coil having a maximum outer diameter of 10 cm or less, and a configuration such that the ratio of the coil's length to its outer diameter is 0.9 or more, and the ratio of the coil's inner diameter to its outer diameter is 0.6 or more, wherein each induction coil in embodiments comprises a magnetic core; and a detection circuit coupled to each coil and configured to convert a current or voltage generated in the coil by a time varying magnetic field to an output signal for use to analyse the time varying magnetic field.

According to a second aspect of the technology described herein there is provided a method of analysing the magnetic field of a region of a subject's body, the method comprising:

using one or more induction coils to detect the time varying magnetic field of a region of a subject's body, each coil having a maximum outer diameter of 10 cm or less, and a configuration such that the ratio of the coil's length to its outer diameter is 0.9 or more, and the ratio of the coil's inner diameter to its outer diameter is 0.6 or more, wherein each induction coil in embodiments comprises a magnetic core;

converting a current or voltage generated in each coil by the time varying magnetic field of the region of a subject's body to an output signal; and using the output signal or signals from the coil or coils to analyse the magnetic field generated by the region of a subject's body.

According to a third aspect of the technology described herein, there is provided a coil for use to detect the time varying magnetic field of a region of a subject's body, the coil comprising:

an induction coil having a maximum outer diameter of 10 cm or less, and a configuration such that the ratio of the coil's length to its outer diameter is 0.9 or more, and the ratio of the coil's inner diameter to its outer diameter is 0.6 or more; and in embodiments a magnetic core.

The technology described herein provides a method and apparatus for detecting and analysing magnetic fields that are medically useful or that could be used as an aid to forming a medical diagnosis, such as the magnetic field of a region of a subject's body (for example of a subject's heart). However, in contrast to existing medical (e.g. cardiac) magnetometer designs, the technology described herein uses an induction coil or coils (i.e. a coil that is joined to an amplifier at both ends) of a specific configuration to detect the magnetic field of the subject (e.g. of the subject's heart). As will be discussed further below, the Applicants have found that induction coils having the particular configuration of the technology described herein can be used to provide a medical magnetometer that can be portable, relatively inexpensive, usable at room temperature and without the need for magnetic shielding, and yet can still provide sufficient sensitivity, accuracy and resolution to be medically useful.

By limiting the outer diameter of the coil to 10 cm or less, a coil having an overall size that can achieve a spatial resolution that is suitable for medical magnetometry (and in particular for magneto cardiography) is provided.

Setting the ratio of the coil's length to its outer diameter to 0.9 or more effectively means that the coil is relatively long (along its axis) for its width, e.g. compared to a Brooks coil configuration (for a Brooks coil this ratio is 0.25) and compared with the arrangement described in WO2014/006387 (for which this ratio is 0.69). Setting the ratio of the coil's inner diameter to its outer diameter to 0.6 or more means that the coil's windings are closely packed in the direction orthogonal to the coil's axis (i.e. have a relatively narrow spread of radial distances from the coil's axis in the direction orthogonal to the coil's axis), e.g. compared to a Brooks coil configuration (for which this ratio is 0.5) and compared with the arrangement described in WO2014/006387 (for which this ratio is 0.425).

As will be described in more detail below, these requirements for the induction coil's configuration have been found by the Applicants to make the coil of the technology described herein particularly sensitive to biological magnetic fields such as in particular the magnetic field of the heart. In particular, the Applicants have found that these requirements make the coil particularly sensitive where the induction coil comprises a soft magnetic core. This is in contrast with the arrangement described in WO2014/006387, which is in effect optimised for induction coils that do not include a magnetic core (e.g. that are air-cored).

It will be appreciated therefore that the technology described herein provides an improved magnetometer system for medical use.

The magnetometer system of the technology described herein can be used as a system and probe to detect any desired magnetic field produced by a subject (by the human (or animal) body). It is in embodiments used to detect (and analyse) the time varying magnetic field of (or produced by) a region of the subject's body, such as their bladder, abdomen, chest or heart, head or brain, muscle(s), womb or one or more foetuses. Thus it may be, and is in embodiments, used to detect magnetic fields relating to the bladder, pregnancy, muscle activity, the brain, or the heart. In various embodiments, the magnetometer is used for (and configured for) one or more of: magnetocardiography, magnetoencephalography, analysis and detection of bladder conditions (e.g. overactive bladder), analysis and detection of foetal abnormalities, and detection and analysis of pre-term labour.

In various particular embodiments the magnetometer is used as a cardiac magnetometer and to detect and analyse the magnetic field of a subject's heart.

Thus, according to another aspect of the technology described herein there is provided a cardiac magnetometer system for analysing the magnetic field of a subject's heart, comprising:

one or more induction coils for detecting the time varying magnetic field of a subject's heart, each coil having a maximum outer diameter of 10 cm or less, and a configuration such that the ratio of the coil's length to its outer diameter is 0.9 or more, and the ratio of the coil's inner diameter to its outer diameter is 0.6 or more, wherein each induction coil in embodiments comprises a magnetic core; and a detection circuit coupled to each coil and configured to convert a current or voltage generated in the coil by the time varying magnetic field of a subject's heart to an output signal for use to analyse the magnetic field generated by the subject's heart.

According to another aspect of the technology described herein there is provided a method of analysing the magnetic field of a subject's heart, the method comprising:

using one or more induction coils to detect the time varying magnetic field of a subject's heart, each coil having a maximum outer diameter of 10 cm or less, and a configuration such that the ratio of the coil's length to its outer diameter is 0.9 or more, and the ratio of the coil's inner diameter to its outer diameter is 0.6 or more, wherein each induction coil in embodiments comprises a magnetic core;

converting a current or voltage generated in each coil by the time varying magnetic field of the subject's heart to an output signal; and using the output signal or signals from the coil or coils to analyse the magnetic field generated by the subject's heart.

According to another aspect of the technology described herein, there is provided a coil for use to detect the time varying magnetic field of a subject's heart, the coil comprising:

an induction coil having a maximum outer diameter of 10 cm or less, and a configuration such that the ratio of the coil's length to its outer diameter is 0.9 or more, and the ratio of the coil's inner diameter to its outer diameter is 0.6 or more; and in embodiments a magnetic core.

As will be appreciated by those skilled in the art, these aspects of the technology described herein can and in embodiments do include any one or more or all of the optional features of the technology described herein described herein, as appropriate.

The magnetometer system of the technology described herein may comprise a single coil. In this case, the coil may be positioned appropriately over a subject (e.g. a subject's chest or other region of the subject's body) to take readings from a suitable (single) sampling position for the region of the subject's body in question. Alternatively, the coil may be moved over the subject (e.g. the subject's chest) to take readings from plural different sampling positions in use.

However, in embodiments, the system comprises plural coils, e.g. and in embodiments at least 7, e.g. 7-500 (or more), in embodiments at least 16, e.g. 16-500 (or more) coils.

Where the magnetometer system comprises plural coils, some or all of the coils may be arranged in a two or three dimensional array, e.g. and in embodiments at least 7, in embodiments at least 16, coils arranged in a two or three dimensional array. In this case, the or each coil array is in embodiments configured such that when positioned appropriately over a subject (e.g. a subject's chest or other region of the subject's body) the coil array can take readings from a suitable set of sampling positions without the need to further move the array over the subject.

The or each array can have any desired configuration, such as being a regular or irregular array, a hexagonal, rectangular or circular array (e.g. formed of concentric circles), etc.

The number and/or configuration of coils in the or each array is in embodiments selected so as to provide an appropriate number of sampling points and/or an appropriate coverage for the region of the subject's body in question.

In various embodiments, the coil array is configured to cover a region of biomagnetic interest, such as the torso or heart. In embodiments, where the magnetometer is used as a cardiac magnetometer to detect and analyse the magnetic field of a subject's heart, the or each array comprises a hexagonal array of at least 7, e.g. 7-50 (or more), in embodiments at least 16, e.g. 16-50 (or more) coils.

An increased number of coils may be provided, e.g. where it is desired to measure the time-varying magnetic field of a subject's heart with a higher resolution and/or where it is desired to measure the time-varying magnetic field of a region of a subject's body other than the heart, such as in particular the brain. According to various embodiments, the or each array may comprise a hexagonal array of 7, 19, 37, 61, 91, 127, 169, 217, 271, 331, 397 (or more) coils.

The magnetometer system may comprise a single layer of coils, or may comprise plural layers of one or more coils, e.g. and in embodiments 2-10 (or more) layers, i.e. one above the other.

In one such embodiment, each coil layer comprises a single coil. In this case, then again, the magnetometer may be positioned appropriately over a subject (e.g. a subject's chest or other region of the subject's body) to take readings from a suitable (single) sampling position for the region of the subject's body in question. Alternatively, the magnetometer may be moved over the subject (e.g. the subject's chest) to take readings from plural different sampling positions in use. However, in various embodiments, one or more or all of the coil layers comprise plural coils, e.g. arranged in a two dimensional array, with one or more or each array in embodiments arranged as discussed above for the two dimensional array arrangement.

In these embodiments, one or more or each coil in each coil layer may be aligned with one or more or each coil in one or more or all of the other layers or otherwise (e.g. anti-aligned), as desired.

Where the magnetometer system comprises plural coils, some or all of the coils may be connected, e.g. in parallel and/or in series. Connecting plural coils in series will have the effect of increasing the induced voltage for a given magnetic field strength. Connecting plural coils in parallel will have the effect of reducing the thermal noise (Johnson noise) in the coils. In embodiments, a combination of series and parallel connections is used to optimise the balance of voltage and noise performance of the coils.

In an embodiment, one or more or each coil in the magnetometer system is arranged in a gradiometer configuration, i.e. where two coils are co-axially aligned (in the direction orthogonal to the plane in which each coil's windings are arranged), and where the signal from each of the coils is summed, e.g. to provide a measure of a change in the magnetic field in space.

The or each coil in the magnetometer system may comprise any suitable coil for detecting a time varying magnetic field.

The or each coil is in embodiments configured to be sensitive at least to magnetic signals between 0.1 Hz and 1 kHz, as this is the frequency range of the (majority of the) relevant magnetic signals of the heart. The or each coil may be sensitive magnetic signals outside of this range. The or each coil is in embodiments sensitive to magnetic fields in the range 10 fT-100 pT.

In the technology described herein, an induction coil or coils (i.e. a coil that is joined to an amplifier at both ends) is used to detect the magnetic field of the subject (e.g. of the subject's heart). Each coil should (and in embodiments does) comprise one or more windings (e.g. wire) arranged in a coil configuration, e.g. comprising multiple turns of wire.

Any suitable conductor can be used for the coil's winding(s), such as copper, aluminium, silver, gold, and alloys and/or platings thereof, etc. However, in various particular embodiments, the coil winding(s) comprises aluminium, in embodiments copper clad aluminium. It would also be possible for the coil winding(s) to comprise silver clad aluminium or gold clad aluminium. The use of aluminium has the effect of reducing the weight of the coil, and therefore the weight of the overall magnetometer system. Furthermore, the addition of copper (or silver or gold) cladding facilitates production by allowing traditional soldering techniques to be employed without the need for the aggressive fluxes that are typically needed for pure aluminium wire.

The total number of turns, N, on the or each coil can be selected as desired. A particular number of turns for the or each coil is 1000 to 10,000, in embodiments 5,000. However, it would be possible for the or each coil to have more turns than this, e.g. up to 50,000 turns, or up to 100,000 turns, etc.

In various embodiments, each coil comprises multiple layers of turns (i.e. rather than only a single layer of turns). This has the effect of increasing the total number of turns, N, and therefore the coil's inductance, L, e.g. without increasing the coil's length, l. Each coil may comprise any plural number of layers, such as at least 2 layers, e.g. 2-50 (or more) layers, in embodiments at least 10 layers, e.g. 10-50 (or more) layers, in embodiments at least 20 layers, e.g. 20-50 (or more) layers, in embodiments around 30 layers of turns. Thus, in various embodiments, each coil comprises a multi-layer coil.

Each coil may be configured as desired. As discussed above, the coil's length, l, its outer diameter, D, and the coil's inner diameter, $D_i$, are carefully selected in the technology described herein.

Each coil has a maximum outer diameter, D, of 10 cm or less, in embodiments 7 cm or less, in embodiments between 1 and 6 cm, in embodiments between 2 and 5 cm.

Although increasing the outer diameter, D, of the coil in general has the effect of increasing the coil's inductance, L, by limiting the outer diameter of the coil to 10 cm or less, a coil having an overall size that can achieve a spatial resolution that is suitable for medical magnetometry (and in particular for magneto cardiography) is provided. In particular, this facilitates a medically applicable diagnostic using 16 to 50 sampling positions (detection channels) to generate an image. (As discussed above, the data for each sampling position can, e.g., be collected either by using an array of coils, or by using one (or several) coils that are moved around the chest to collect the data.)

In addition, limiting the coil's outer diameter to 10 cm or less limits its weight (and therefore the overall weight of the magnetometer system), and ensures that the coil is practical and wieldy for use in a magnetometer system.

In the technology described herein, the ratio of the coil's length to its outer diameter, l:D, is 0.9 or more, in embodiments 0.95 or more, in embodiments 1 or more. It would also be possible for the ratio of the coil's length to its outer diameter, l:D, to be ≥2, ≥3, etc. In various embodiments, the ratio of the coil's length to its outer diameter, l:D, is also less than 3, in embodiments less than 2.5, in embodiments less than 2, in embodiments less than 1.5. Thus, in various embodiments, the ratio of the coil's length to its outer diameter, l:D, is in the range 0.9 to 3.

Setting the ratio of the coil's length to its outer diameter to at least 0.9 effectively means that the coil is relatively long (along its axis) for its width, e.g. compared to a Brooks coil configuration (for a Brooks coil this ratio is 0.25) and compared with the arrangement described in WO2014/006387 (for which this ratio is 0.69). This means that the coil can (and in embodiments does) comprise more turns of wire for a given outer diameter, and thereby increases the coil's inductance, L. This arrangement is also particularly beneficial when the coil comprise a magnetic core, as will be described in more detail below.

Each coil may have any suitable length, l (i.e. coil winding(s) length). Each coil in embodiments has a length, l, of 10 cm or less, in embodiments between 1 and 10 cm, in embodiments between 3 and 7 cm, in embodiments between 4 and 6 cm. In particular embodiments each coil has a length, l, of substantially 5 cm.

In this regard, the Applicants have recognised that although increasing the length, l, (of the windings(s)) of the coil means that the coil can comprise more turns of wire and can accordingly increase its inductance, L, the benefits of increasing the length (of the windings(s)) of the coil do not increase linearly as the coil's (winding's) length increases, but instead fall off as the coil's (winding's) length increases. This is because the biological magnetic fields of interest are relatively small, and because the magnetic field strength is inversely proportional to the cube of the distance ($1/r^3$), e.g. from the region of the subject's body (e.g. heart). This means that turns at the "top" of the coil will experience a different magnetic field strength to those at the "bottom". In addition to this, smaller coils are lighter, and are more practical and wieldy for a useful magnetometer system.

As such, the Applicants have found that by limiting the length (of the windings(s)) of the coil to 10 cm or less, in embodiments between 1 and 10 cm, in embodiments between 3 and 7 cm, in embodiments between 4 and 6 cm, in particular embodiments to substantially 5 cm, a coil that is sufficiently sensitive to biological magnetic fields, and that has an overall size and weight that can be used in a practical arrangement for medical magnetometry (and in particular for magneto cardiography) is provided.

In the technology described herein, the ratio of the coil's inner diameter to its outer diameter (i.e. the ratio of the inner diameter of the winding(s) to the outer diameter of the winding(s)), $D_i:D$, is 0.6 or more. Setting the ratio of the coil's inner diameter to its outer diameter to 0.6 or more means that the coil's winding(s) are packed relatively tightly in the direction orthogonal to the core's axis (i.e. have a relatively narrow spread of radial distances from the coil's axis in the direction orthogonal to the coil's axis), e.g. compared to a Brooks coil configuration (for which this ratio is 0.5) and compared with the arrangement described in WO2014/006387 (for which this ratio is 0.425).

In this regard, the Applicants have recognised that the inductance per turn will not in general be constant for all turns of a (multi-layer) coil. This is because, e.g., the turns of an outer layer of a (multi-layer) coil will have a greater diameter than the turns of an inner layer of the coil, and so the turns of the outer layer will typically provide a higher inductance per turn. The Applicants have furthermore recognised that it can be beneficial for the coil to have a relatively consistent inductance per turn (this can, e.g., reduce distortion), and that this can be achieved by ensuring that the ratio of coil's inner diameter to its outer diameter, $D_i:D$, is as close to one as possible (i.e. by ensuring that the turns have as narrow a spread of radial distances from the coil's axis in the direction orthogonal to the coil's axis as possible). This arrangement is also particularly beneficial when the coil comprises a magnetic core, as will be described in more detail below.

On the other hand, as described above, the coil should comprise plural layers of turns, and increasing the number of layers of turns has the effect of increasing the coil's inductance (e.g. without increasing the coil's length, l). However, increasing the number of layers of turns will decrease the ratio of the coil's inner diameter to its outer diameter, $D_i:D$.

In this regard, the Applicants have found that a particularly beneficial balance can be found between these competing factors by providing a coil or coils with an inner to outer diameter ratio, $D_i:D$, of 0.6:1 or more, and moreover that this arrangement provides a suitably sensitive multi-layer coil for which the inductance per turn is relatively consistent.

In various particular embodiments, the ratio of the coil's inner diameter to its outer diameter, $D_i:D$, is 0.625 or more, in embodiments 0.65 or more, 0.675 or more, 0.7 or more, 0.725 or more, and/or 0.75 or more. The ratio of the coil's inner diameter to its outer diameter, $D_i:D$, may also be 0.8 or more, or 0.9 or more.

The ratio of the coil's inner diameter to its outer diameter, $D_i:D$, should also be (by definition) less than 1. (The upper limit for this ratio is where the coil comprises a single layer of wire.) Thus, the ratio of the coil's inner diameter to its outer diameter, $D_i:D$, is in embodiments in the range 0.6:1 to ~1:1. In various embodiments, the ratio of the coil's inner diameter to its outer diameter, $D_i:D$, is also less than 0.9, in embodiments less than 0.8.

In various particular embodiments, the or each coil has the following configuration:

$$4 \text{ cm} \leq D \leq 5 \text{ cm};$$
$$l \approx 5 \text{ cm; and}$$
$$\frac{Di}{D} \approx 0.745$$

where D is the outer diameter of the coil, l is length of the coil, and $D_i$ is the inner diameter of the coil.

In various other particular embodiments, the or each coil has the following configuration:

$$4 \text{ cm} \leq D \leq 5 \text{ cm};$$
$$l \approx 5 \text{ cm; and}$$
$$\frac{Di}{D} \approx 0.625$$

where D is the outer diameter of the coil, l is length of the coil, and $D_i$ is the inner diameter of the coil.

Coils having these proportions have been found to have a particularly high inductance, L, and sensitivity to biological magnetic fields of interest.

In various embodiments, a relatively small wire radius is used for the coil winding(s). This allows the coil to have more layers of turns while maintaining a relatively high inner to outer diameter ratio, $D_i:D$. A particular wire radius is 1 mm or less, in embodiments 0.5 mm or less, in embodiments 0.4 mm or less, in embodiments 0.3 mm or less, in embodiments 0.25 mm or less, in embodiments 0.2 mm or less, in embodiments 0.15 mm or less, in embodiments 0.1 mm or less.

It should be noted here that the use of a relatively small wire radius goes against the conventional aim of increasing the wire radius to decrease the coil's resistance and noise. In this regard, the Applicants have found that when measuring relatively small biological magnetic fields, such as the magnetic field of the heart, the increased noise can be tolerated because of the benefits derived from using a coil with both a relatively high number of turns, N, and a relatively high inner to outer diameter ratio, $D_i:D$.

In various embodiments, the coil is as tightly-packed as possible, e.g. in both the direction orthogonal to the core's axis, and in the (axial) direction parallel to the core's axis. In embodiments the coil is as close to layer-wound as possible, i.e. not scatter wound. However, it would be possible for the coil to comprise a less tightly wound coil.

The winding density (the ratio of the cross sectional area of the winding to the cross sectional area of the wire) of the coil is in embodiments in the range 0.5 to 1, in particular embodiments 1. Higher winding densities facilitate both a relatively high number of turns N and a relatively high inner to outer diameter ratio, $D_i:D$. In other words, tighter windings improve the performance of the coil (whereas gaps can introduce losses).

Each coil may have a magnetic core (i.e. the coil windings may be wound around a magnetic core). In various particular embodiments, a soft magnetic core is used. Providing each coil with a magnetic core increases the inductance, L, of the coil. Thus, in various embodiments each coil comprises a soft magnetic core.

In this regard, the Applicants have found that the requirements for the induction coil's configuration of the technology described herein make the coil particularly sensitive where the induction coil comprises a magnetic core. This is in contrast with the arrangement described in WO2014/006387, which is in effect optimised for induction coils that do not include a magnetic core (e.g. that are air-cored).

Any suitable magnetic core material may be used such as a ferromagnetic material (e.g. iron), a ferrite or another magnetic material. In embodiments the core comprises a soft magnetic material such as a soft ferrite.

In various particular embodiments, the magnetic core is made from a material with a high relative permeability, $\mu_r$, e.g. at least 10, in embodiments at least 1,000 in embodiments at least 10,000, in embodiments at least 100,000. The higher the relative permeability, $\mu_r$, of the core material, the higher the inductance, L, of the coil.

Suitable high relative permeability materials include, for example, carbon steel ($\mu_r \approx 100$), ferrites such as Nickel Zinc ($\mu_r \approx 16$ to 640), Manganese Zinc ($\mu_r > 640$), pure iron or steel. In embodiments, the magnetic core is made from higher relative permeability materials such as magnetic amorphous metal alloys such as Metglas 2714a ($\mu_r > 80,000$ (e.g. unannealed) to ~1,000,000 (e.g. annealed)), nano-crystalline material such as FINEMET ($\mu_r > 80,000$ (e.g. unannealed) to ~200,000 (e.g. annealed)), nickel-iron alloys such as Mu-metal ($\mu_r \approx 20,000$ to 80,000), cobalt iron alloys, and the like. These materials can exhibit very high magnetic permeabilities, but can be lighter than other magnetic materials such as iron powder. This can beneficially reduce the overall weight of the magnetometer system.

Each magnetic core in embodiments comprises a cylinder of (soft) magnetic material, and is in embodiments located within the winding(s) of the coil. Thus, the core in embodiments has an outer diameter, $D_c$, less than or equal to the inner diameter $D_i$ of the coil (winding(s)).

In various particular embodiments, the core has an outer diameter, $D_c$, that is close to or equal to the inner diameter, $D_i$, of the coil windings. Thus, the ratio of the core's outer diameter to the inner diameter of the coil, $D_c:D_i$, is in embodiments 1 or as close to 1 as possible, e.g. 0.8 or more, in embodiments 0.9 or more, in embodiments 0.95 or more, in embodiments 0.99 or more. In this regard, the Applicants have found that the core's effect of increasing the coil's inductance, L, is greater when the core is closer to the coil's winding(s).

In particular embodiments the outer surface of the core is arranged to be in contact with the coil winding(s), e.g. for at least part (in embodiments most or all) of its circumference. Arranging for the outer surface of the core to be in contact with the coil winding(s) means that the winding(s) are as close as possible to the core, and accordingly that the core's effect of increasing the coil's inductance, L, is as large as possible. It should be noted that this goes against the conventional teaching of providing an air gap between the core and the coil winding(s) to reduce the possibility of saturation in high magnetic fields. In this regard, the Applicants have recognised that the risk of saturation is very low in the context of medical magnetometry, since e.g. biological magnetic field strengths are relatively small.

(It is not, however, necessary for the core to be in direct contact with the windings. For example, there may be one or more of a (air) gap, an insulation layer, an adhesive layer or otherwise between the core and the wire of the winding(s).)

Each core may be solid, e.g. may comprise a solid cylinder (of (soft) magnetic material). However, in various embodiments, each core is at least partially hollow, e.g. comprises a hollow cylinder (of (soft) magnetic material). In this regard, the Applicants have found that the use of a hollow core does not significantly reduce the inductance, L, of the coil, but can significantly reduce the coil's weight, as well as its cost.

In these embodiments, the percentage of the cross-sectional area of the core that is hollow (i.e. that is occupied by a hole) can be selected as desired, e.g. in embodiments 25% or more, in embodiments 50% or more, in embodiments 75% or more, in embodiments 90% or more. Although increasing the size of the hole in the hollow core can increase the risk of saturation, it beneficially reduces the overall cost and weight of the coil. The hollow core may have any suitable thickness, such as a few mm or less, in embodiments around 1 mm or less.

Equally, the hollow core may be formed in any suitable manner. In various particular embodiments, the core comprises one or more sheets of magnetic material, e.g. that are formed into a hollow cylinder. The one or more sheets may be formed into a hollow cylinder, for example, by rolling up one or more sheets, and/or by laminating multiple sheets together. In these embodiments, the or each sheet may have any suitable thickness, such as a few mm or less, ≤1 mm, ≤500 μm, ≤100 μm, ≤75 μm, ≤50 μm, and/or ≤25 μm. In various particular embodiments, the core comprises a 35 μm sheet of Metglas 2714a.

The hollow core may comprise a single layer of magnetic material or multiple layers of magnetic material (e.g. where the sheet of magnetic material is rolled around itself multiple times and/or where the core comprises multiple laminated layers of magnetic material). Where the hollow core comprise multiple layers, any suitable number of layers may be used, such as 2, 3, 4, 5 or more layers of magnetic material.

Thus, in various embodiments, the core comprises one or more rolled sheets of (soft) magnetic material. This represents a particularly convenient, low cost and low weight core arrangement.

As described above, the core is in embodiments made from a material having a high relative permeability, $\mu_r$ (because increasing the core's relative permeability increases the coil's inductance). The Applicants have furthermore recognised that the effective permeability, $\mu_e$, of the core is determined both by the relative permeability, $\mu_r$, of the core material and the geometry of the core. In particular, the effective permeability, $\mu_e$, of the core is determined by the ratio of the core's length to its diameter, $l_c:D_c$. Thus, in various embodiments, the core's outer diameter, $D_c$, and its length, $l_c$, are carefully selected.

In various particular embodiments, the ratio of the core's length to its diameter, $l_c:D_c$, is >1, in embodiments >1.5, in embodiments >2. It would also be possible for the ratio of the core's length to its diameter, $l_c:D_c$, to be larger than this, e.g. >3. In this regard, the Applicants have recognised that, in general, increasing the ratio of the core's length to its diameter, $l_c:D_c$, has the effect of increasing the core's effective permeability, $\mu_e$, and therefore the coil's inductance, L. This is particularly the case for magnetic materials with a high relative permeability (e.g. as described above), for which these benefits are highly nonlinear. (Materials with a low relative permeability do not benefit as much, if at all, from increasing this aspect ratio). The ratio of the core's length to its diameter, $l_c:D_c$, is limited by practicality and size considerations. Thus, in various embodiments, the ratio of the core's length to its diameter, $l_c:D_c$, is also <3.

In order to increase the ratio of the core's length to its diameter, $l_c:D_c$, either the core's length, $l_c$, can be increased, and/or its diameter, $D_c$, can be decreased.

In this regard, it would be possible for the core's length, $l_c$, to be less than the length, l, of the coil's winding(s). However, in various embodiments, the core has a length, $l_c$, that is greater than or equal to the length, l, of the coil's winding(s).

Arranging for the core's length, $l_c$, to be equal to the length, l, of the winding(s) means that the core's length, $l_c$, is as long as possible (and that the core's length to diameter ratio, $l_c:D_c$, is as large as possible) for a given coil winding length, l, without increasing the overall (total) length of the coil.

Arranging for the core's length, $l_c$, to be greater than the length, l, of the winding(s) can allow the core's length to diameter ratio, $l_c:D_c$, to be further increased, e.g. at the expense of increasing the overall length of the coil. In this regard, the Applicants have recognised that the overall (total) length of the coil (i.e. the length including the winding(s) and the core) should be (and is in embodiments) 30 cm or less, in embodiments between 1 and 10 cm, in embodiments between 3 and 7 cm, in embodiments between 4 and 6 cm, in particular embodiments to substantially 5 cm. This results in a practical and wieldy coil for use in a magnetometer system.

Thus, each core in embodiments has a length, $l_c$, of 30 cm or less, in embodiments between 1 and 10 cm, in embodiments between 3 and 7 cm, in embodiments between 4 and 6 cm. In particular embodiments each core has a length, $l_c$, of substantially 5 cm.

It should be noted here that setting the ratio of the coil's length to its outer diameter to 0.9 or more, i.e. so that the coil is relatively long (along its axis) for its width (as described above), means that the coil can (and in embodiments does) comprise a magnetic core that has a relatively large length to diameter ratio, $l_c:D_c$, (and accordingly a high effective permeability, $\mu_e$), and accordingly that the coil will have a relatively high inductance, L.

In contrast with increasing the core's length, $l_c$, and as will be described in more detail below, decreasing the core's diameter, $D_c$, (i.e. to increase the ratio of the core's length to its diameter, $l_c:D_c$) can lead away from a number of the other particular parameters described above.

In particular, as described above, it is preferable for the coil's inner to outer diameter ratio, $D_i:D$, to be relatively large (i.e. 0.6 or more, and in embodiments as close to 1 as possible), and this is particularly the case where the coil comprises a magnetic core. This is because, as recognised by the Applicants, the magnetic core's effect of increasing the coil's inductance is not in general constant for all the coil's turns. In particular, the turns of the inner layers of the coil, i.e. that are closer to the core than the turns of the outer layers of the coil, will experience a significantly larger increase in inductance per turn due to the presence of the core than the turns of the outer layers. As such, in order to maximise the effect of the core, the turns of all of the layers of the coil should be relatively close to the core (and so the coil's inner to outer diameter ratio, $D_i:D$, should be relatively large). (For the same reason, and as described above, it is preferable for the outer diameter of the core, $D_c$, to be as close as possible to the inner diameter $D_i$, of the coil.)

However, decreasing the core's outer diameter, $D_c$, while maintaining the outer surface of the core in close proximity with the inner surface of the windings, and while maintaining a relatively high coil inner to outer diameter ratio, $D_i:D$, (i.e. so that the turns of the coil are all in relative close proximity to the core) could result in a core with a reduced outer diameter D. As described above, reducing the outer diameter D of the core would, in turn, be expected to reduce the overall inductance, L, of the coil.

In this regard, the Applicants have found that a particularly beneficial balance between the above described factors is found where the inner to outer diameter ratio, $D_i:D$, is 0.6 or more, in embodiments between 0.6 and 0.8, in embodiments between 0.6 and 0.7. In particular embodiments, the coil's inner to outer diameter ratio, $D_i:D$, is substantially 0.625. The Applicants have found that for coils that include a core, these proportions provide a particularly high inductance.

Thus, in various particular embodiments, the or each coil has the following configuration:

$$D \approx 4 \text{ cm};$$
$$l \approx 5 \text{ cm}; \text{ and}$$
$$\frac{Di}{D} \approx 0.625$$

where D is the outer diameter of the coil, l is length of the coil, and $D_i$ is the inner diameter of the coil, and comprises a magnetic core having the following configuration:

$D_c \approx 2.5$ cm; and
$l_c \approx 5$ cm;

where $D_c$ is the outer diameter of the core, and $l_c$ is the length of the core. Coils having these proportions have been found to have a particularly high inductance L, and sensitivity to biological magnetic fields of interest.

The detection circuit that a coil is coupled to and that is used to detect the output from the coil should, as discussed above, generate an appropriate output signal for analysis from the voltage and/or current that is induced in the coil by the magnetic field. Any suitable detection circuit and arrangement that can do this can be used. In embodiments the detection circuit converts the voltage or current generated in the coil by the magnetic field into a digital signal for post processing and averaging.

Where the system includes plural coils, each coil in embodiments has its own, respective and separate, detection circuit (i.e. there will be as many detection circuits as there are coils). The output signals from the detection circuits can then be combined as desired in post processing.

In various embodiments, each detection circuit operates in either a voltage or current sensing mode (in other words, detects and measures a signal generated between the ends of the coil by a time varying magnetic field).

In various embodiments, the voltages produced by the detection circuit are digitised, e.g. for post processing, noise reduction and signal recovery. Digitisation of the output voltage as early as possible (practical) in the detection setup is preferred to limit amplifier noise. Thus, in various embodiments, the signal or signals from the one or more coils is or are digitised, e.g. using one or more digitisers.

The or each digitiser may comprise any suitable digitiser that is operable to digitise (convert) an analogue signal received from the one or more coils into a digital signal, e.g. for further processing and averaging, etc. The digitiser should (and in embodiments does) convert a voltage or current generated in the one or more coils by the magnetic field into a digital signal. In various embodiments, the or each digitiser comprises an analogue to digital converter (ADC).

In various embodiments, the magnetometer system comprises a digitiser coupled to each coil and configured to digitise a signal from the coil. Where the system includes plural coils, each coil may have its own, respective and separate, digitiser (i.e. there will be as many digitisers as there are coils), or some or all of the coils may share a digitiser.

The or each digitiser may be directly connected to the or each respective coil, or in embodiments, the or each digitiser may be connected to the or each respective coil via an amplifier. Thus in various embodiments, the magnetometer system includes one or more detection amplifiers, in embodiments in the form of a microphone amplifier (a low impedance amplifier), connected to one or more or each coil, e.g. to the ends of each coil. The or each detection amplifier is in embodiments then connected to a digitiser or digitisers.

The or each amplifier may be configured to have any suitable and desired amplification level. The or each amplifier may, for example, amplify the signal (including the noise) received from the or each coil by around 1000 times (60 dB) or more.

In various embodiments, the magnetometer system is arranged such that the coil and amplifier (that is coupled to the coil) are arranged together in a sensor head or probe which is then joined by a wire to the remaining components of the magnetometer system to allow the sensor head (probe) to be spaced from the remainder of the magnetometer system in use.

In various embodiments, the (in embodiments digitised) signal or signals from the one or more coils, are averaged over plural periods, e.g. using averaging circuitry. The digitised signal or signals may be averaged over plural periods as desired, and the averaging circuitry may comprise any suitable and desired circuitry for averaging the digitised signal or signals over plural periods.

In an embodiment, a trigger is provided and used for gating (windowing) the signal (i.e. for identifying and dividing the periodic or pseudo periodic signal into its plural repeating periods). The trigger should be, and in embodiments is, synchronised with the time varying magnetic field of the region of the subject's body. For example, where the magnetometer is used to analyse the magnetic field of a subject's heart, then the signal is in embodiments averaged over a number of heart beats, and an ECG or Pulse Ox trigger from the test subject may be used as a detection trigger for the signal acquisition process.

Thus, in various embodiments, a trigger is used to identify each repeating period of the (periodic or pseudo periodic) signal, and then the signal is averaged over the plural identified periods.

Other arrangements would, of course, be possible. For example, each repeating period of the (periodic or pseudo periodic) signal may be identified without the use of a trigger, and then the signal may be averaged over the plural identified periods.

The (in embodiments digitised) signal or signals from the one or more coils may be filtered, if desired.

In various embodiments, one or more steps are taken to eliminate and/or compensate for any environmental noise or magnetic field interference that may exist in the signal(s) prior to digitisation. Any suitable such techniques may be used (e.g. as described in WO2014/006387), although it should be noted here that the technology described herein does not require the use of a magnetically shielded environment.

Other arrangements would, of course, be possible.

It should also be noted that the Applicants have found that heart beat scale sensitivity can be achieved with the technology described herein without using gradient or background noise subtraction (or any equivalent process to compensate for background noise), although using gradient or background noise subtraction (or an equivalent process) will allow a useful signal to be produced more quickly.

In various embodiments, any remaining environmental noise (where present) may be reduced and/or removed in post processing.

The system and method of the technology described herein can be used as desired to analyse the magnetic field, e.g. of the subject's heart. A heartbeat's waveform and/or information such as a time interval or intervals e.g. between separate heartbeats and/or between certain features within a single heartbeat, and/or a shape or shapes of a heartbeat(s) may be obtained from the output signal or signals. In embodiments, suitable measurements are taken to allow an appropriate magnetic scan image of the heart (or other body region of interest) to be generated, which image can then, e.g., be compared to reference images for diagnosis. The technology described herein can be used to carry out any suitable procedure for imaging the magnetic field of the heart.

In embodiments plural (e.g. 7 to 500 (or more) (e.g. as described above)) sampling positions (detection channels) are detected in order to generate the desired scan image.

The technology described herein accordingly extends to the use of the magnetometer system of the technology described herein for analysing, and in embodiments for imaging, the magnetic field generated by a subject's heart (or other body region), and to a method of analysing, and in embodiments of imaging, the magnetic field generated by a subject's heart (or other body region) comprising using the method or system of the technology described herein to analyse, and in embodiments to image, the magnetic field generated by a subject's heart (or other region of the body). The analysis, and in embodiments the generated information and/or image, is in embodiments used for diagnosis of (to diagnose) a medical condition, such as abnormality of the heart, etc.

Thus according to another aspect of the technology described herein, there is provided a method of diagnosing a medical condition, comprising:

using one or more induction coils to detect the time varying magnetic field of a region of a subject's body, each coil having a maximum outer diameter of 10 cm or less, and a configuration such that the ratio of the coil's length to its outer diameter is 0.9 or more, and the ratio of the coil's inner diameter to its outer diameter is 0.6 or more, wherein each induction coil in embodiments comprises a magnetic core;

using a detection circuit or circuits coupled to the coil or coils to convert a current or voltage generated in each coil by the time varying magnetic field of the region of the subject's body to a respective output signal for the coil;

using the output signal or signals from the coil or coils to analyse the magnetic field generated by the region of the subject's body; and using the analysis of the magnetic field generated by the region of the subject's body to diagnose said medical condition.

In this aspect of the technology described herein, the output signal or signals from the coil or coils are in embodiments used to produce an image representative of the magnetic field generated by the region of the subject's body, and the method in embodiments then comprises comparing the image obtained with a reference image or images to diagnose the medical condition. The medical condition is, as discussed above, in embodiments one of: abnormality of the heart, a bladder condition, pre-term labour, foetal abnormalities or abnormality of the head or brain.

As will be appreciated by those skilled in the art, these aspects and embodiments of the technology described herein can and in embodiments do include any one or more or all of the optional features of the technology described herein described herein, as appropriate.

As will be appreciated from the above, a particular advantage of the technology described herein is that it can be used in the normal hospital or surgery or other environment, without the need for magnetic shielding. Thus, in various particular embodiments, the methods of the technology described herein comprise using the magnetometer system to detect the magnetic field of a subject's heart (or other body region) in a non-magnetically shielded environment (and without the use of magnetic shielding). (It would, however, be possible to use the magnetometer system to detect the magnetic field of a subject's heart (or other body region) in a magnetically shielded environment (and with the use of magnetic shielding), if desired.)

Correspondingly, a particular advantage of the technology described herein is that it can be used without the need for cooling such a cryogenic cooling. Thus, in various particular embodiments, the methods of the technology described herein comprise using the magnetometer system to detect the magnetic field of a subject's heart (or other body region) without the use of (e.g. cryogenic) cooling. (It would, however, be possible to use the magnetometer system to detect the magnetic field of a subject's heart (or other body region) with the use of (e.g. cryogenic) cooling, if desired.)

As will be appreciated by those skilled in the art, all of the aspects and embodiments of the technology described herein can and in embodiments do include any one or more or all of the optional features of the technology described herein, as appropriate.

The methods in accordance with the technology described herein may be implemented at least partially using software e.g. computer programs. It will thus be seen that when viewed from further aspects the technology described herein provides computer software specifically adapted to carry out the methods herein described when installed on data processing means, a computer program element comprising computer software code portions for performing the methods herein described when the program element is run on data processing means, and a computer program comprising code means adapted to perform all the steps of a method or of the methods herein described when the program is run on a data processing system. The data processing system may be a microprocessor, a programmable FPGA (Field Programmable Gate Array), etc.

The technology described herein also extends to a computer software carrier comprising such software which when used to operate a magnetometer system comprising data processing means causes in conjunction with said data processing means said system to carry out the steps of the methods of the technology described herein. Such a computer software carrier could be a physical storage medium such as a ROM chip, CD ROM or disk, or could be a signal such as an electronic signal over wires, an optical signal or a radio signal such as to a satellite or the like.

It will further be appreciated that not all steps of the methods of the technology described herein need be carried out by computer software and thus from a further broad aspect the technology described herein provides computer software and such software installed on a computer software carrier for carrying out at least one of the steps of the methods set out herein.

The technology described herein may accordingly suitably be embodied as a computer program product for use with a computer system. Such an implementation may comprise a series of computer readable instructions either fixed on a tangible medium, such as a non-transitory computer readable medium, for example, diskette, CD ROM, ROM, or hard disk. It could also comprise a series of computer readable instructions transmittable to a computer system, via a modem or other interface device, over either a tangible medium, including but not limited to optical or analogue communications lines, or intangibly using wireless techniques, including but not limited to microwave, infrared or other transmission techniques. The series of computer readable instructions embodies all or part of the functionality previously described herein.

Those skilled in the art will appreciate that such computer readable instructions can be written in a number of programming languages for use with many computer architectures or operating systems. Further, such instructions may be stored using any memory technology, present or future, including but not limited to, semiconductor, magnetic, or optical, or transmitted using any communications technology, present or future, including but not limited to optical, infrared, or microwave. It is contemplated that such a computer program product may be distributed as a removable medium with accompanying printed or electronic documentation, for example, shrink wrapped software, preloaded with a computer system, for example, on a system ROM or fixed disk, or distributed from a server or electronic bulletin board over a network, for example, the Internet or World Wide Web.

A number of embodiments of the technology described herein will now be described by way of example only and with reference to the accompanying drawings, in which.

Like reference numerals are used for like components where appropriate in the Figures.

Figure 1:
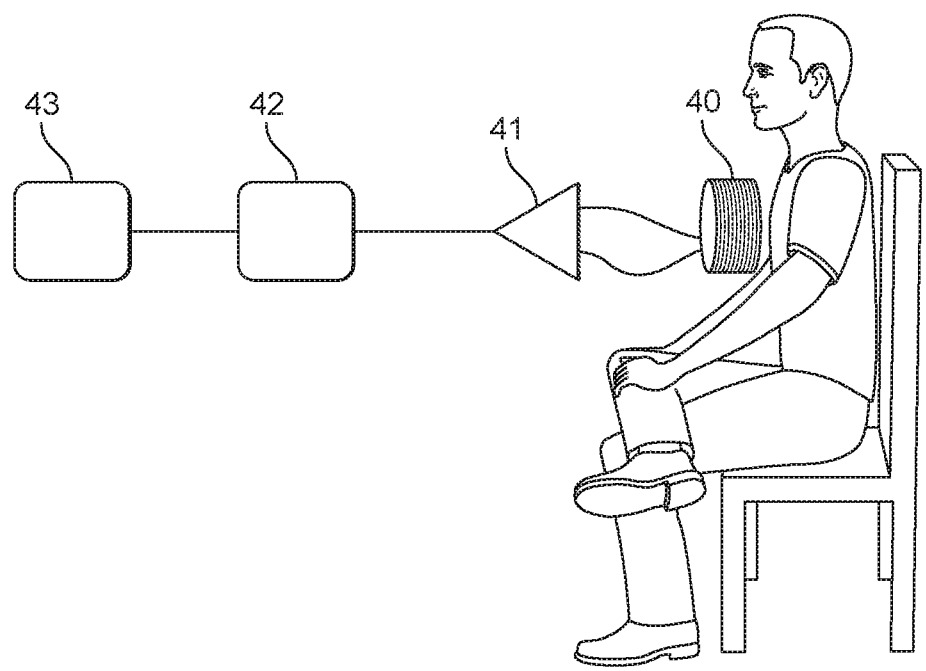
FIG. 1 shows schematically the use of an embodiment of the technology described herein for detecting the magnetic field of a subject's heart.

FIG. 1 shows schematically the basic arrangement of various embodiments of a magnetometer system that may be operated in accordance with the technology described herein. This magnetometer system is specifically intended for use as a cardiac magnetometer (for use to detect the magnetic field of a subject's heart). However, the same magnetometer design can be used to detect the magnetic field produced by other body regions, for example for detecting and diagnosing bladder conditions, pre-term labour, foetal abnormalities and for magnetoencephalography. Thus, although the present embodiment is described with particular reference to cardio-magnetometry, it should be noted that the present embodiment (and the technology described herein) extends to other medical uses as well.

The magnetometer system comprises an induction coil 40 coupled to a detection circuit 41 that may contain a number of components.

The detection circuit 41 may comprise a low impedance pre amplifier, such as a microphone amplifier, that is connected to the coil 40, and one or more filters, e.g. one or more a low pass filters, one or more high pass filters, one or more band pass filters, and/or one or more notch filters e.g. to remove line noise (e.g. 50 or 60 Hz and harmonics).

The current output from the coil 40 is processed and converted to a voltage by the detection circuit 41 and provided to an analogue to digital converter (ADC) 42 which digitises the analogue signal from the coil 40 and provides it to a data acquisition system 43.

A biological signal that is correlated to the heartbeat, e.g. an ECG or Pulse-Ox trigger from the test subject may be used as a detection trigger for the digital signal acquisition, and the digitised signal over a number of trigger pulses is then binned into appropriate signal bins, and the signal bins overlaid or averaged, by the data acquisition unit 43. Other arrangements would, however, be possible.

The coil 40 and detection circuit 41 may be arranged such that the coil 40 and the preamplifier of the detection circuit 41 are arranged together in a sensor head or probe which is then joined by a wire to a processing circuit that comprises the remaining components of the detection circuit 41. Connecting the sensor head (probe) and the processing circuit by wire allows the processing circuit to be spaced from the sensor head (probe) in use.

With this magnetometer, the sensor head (probe) will be used as a magnetic probe by placing it in the vicinity of the magnetic fields of interest.

Figure 2:
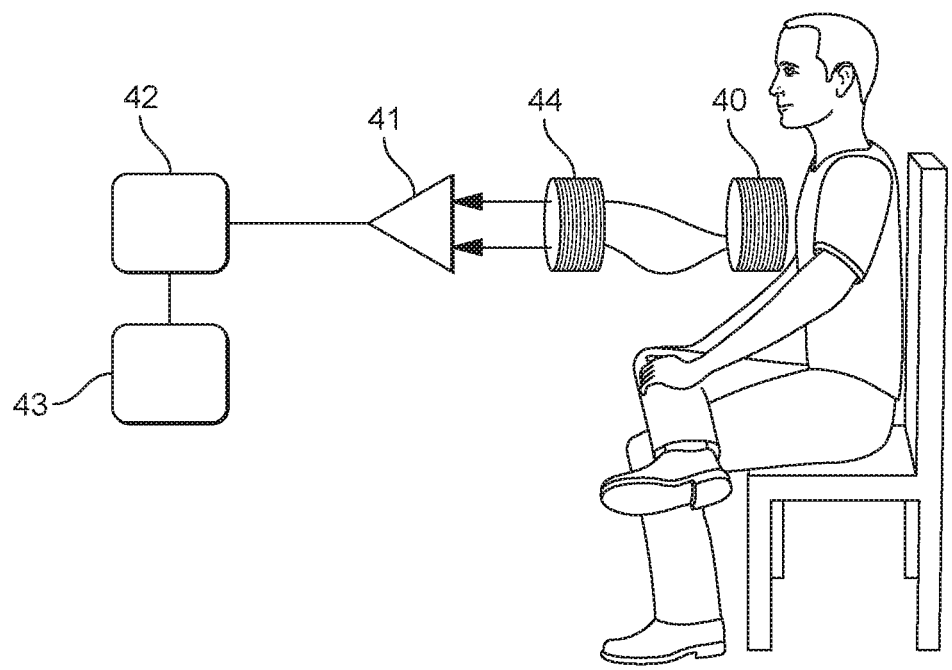
FIGS. 2-5 show further exemplary arrangements of the use of an embodiment of the technology described herein when detecting the magnetic field of a subject's heart.

FIG. 2 shows an improvement over the FIG. 1 arrangement, which uses in particular the technique of gradient subtraction to try to compensate for background noise. (Other techniques could, however, be used). In this case, an inverse coil 44 is used to attempt to subtract the effect of the background noise magnetic field from the signal detected by the probe coil 40. The inverse coil 44 will be equally sensitive to any background magnetic field, but only weakly sensitive to the subject's magnetic field. The inverse coil 44 can be accurately matched to the pickup coil 40 by, for example, using a movable laminated core to tune the performance of the inverse coil to that of the pickup coil 40.

Figure 3:
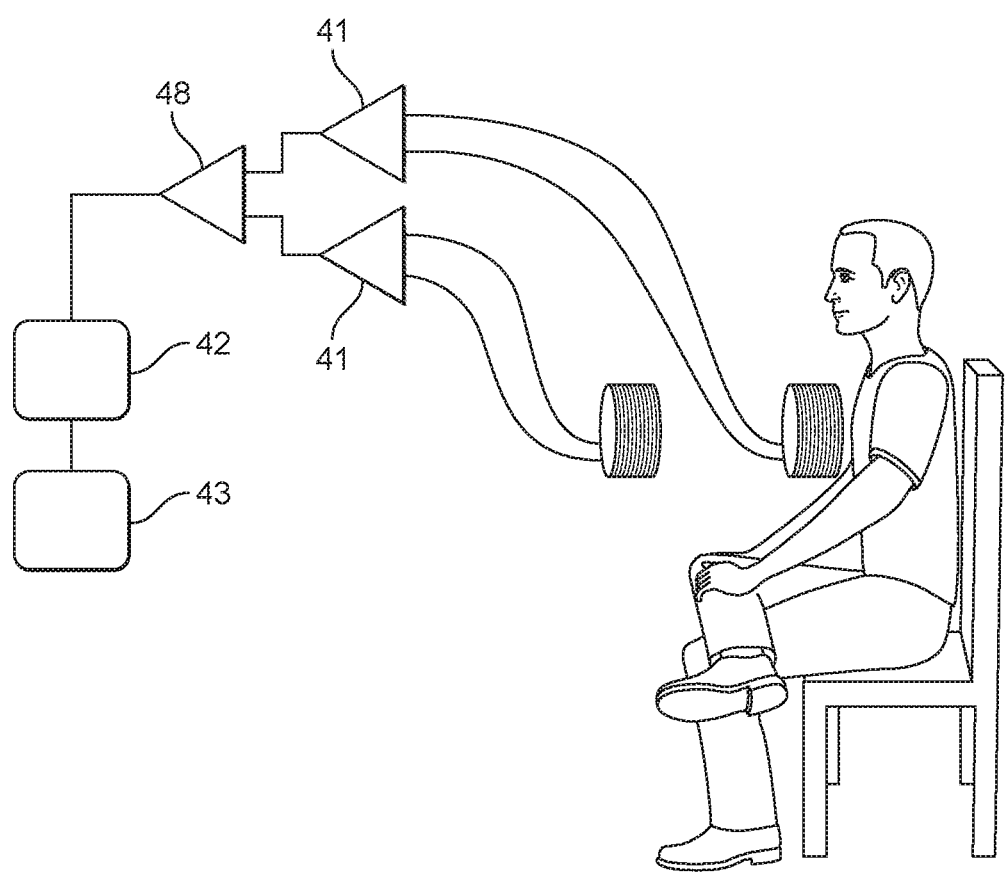

FIG. 3 shows an alternative gradient subtraction arrangement. In this case, both coils 40, 44 have the same orientation, but their respective signals are subtracted using a differential amplifier 45. Again, the best operation is achieved by accurately matching the coils and the performance of the detection circuits 41. Again, a movable laminated core can be used to tune the performance of one coil to match the performance of the other.

Figure 4:
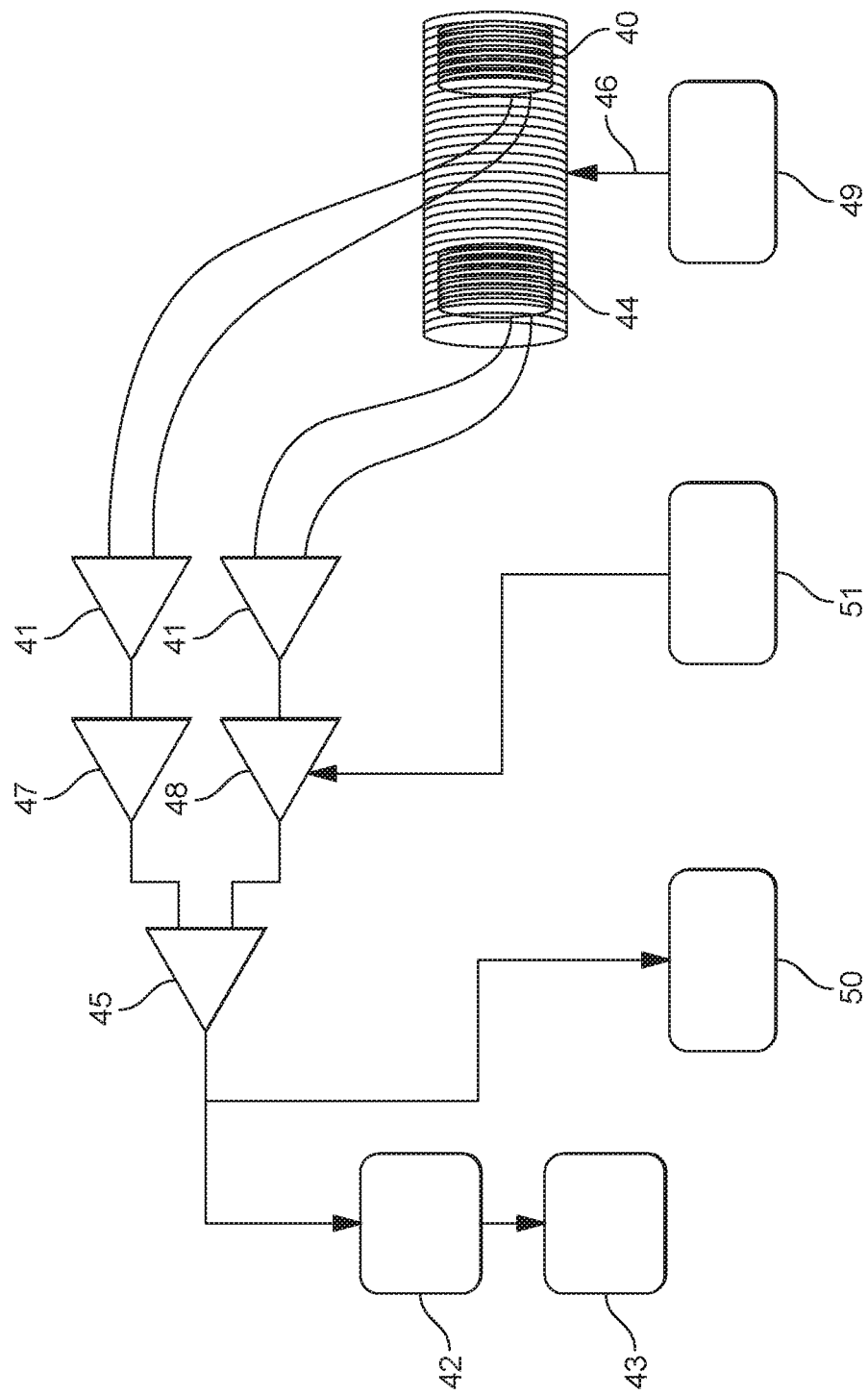

FIG. 4 shows a further embodiment. This circuit operates on the same principle as the arrangement of FIG. 3, but uses a more sophisticated method of field cancellation, and passive coil matching. In particular, a known global magnetic field 44 is introduced to both coils 40, 44 to try to remove background magnetic field interference.

In this circuit, the outputs from the detection circuits 41 are passed through respective amplifiers 47, 48, respectively, before being provided to the differential amplifier 45. At least one of the amplifiers 47, 48 is tuneable. In use, a known global field 46, such as 50 or 60 Hz (and harmonics) line noise, or a signal, such as a 1 kHz signal, applied by a signal generator 49, is introduced to both coils 40, 44.

The presence of a signal on this frequency on the output of the differential amplifier 45, which can be observed, for example, using an oscilloscope 50, will then indicate that the coils 40, 44 are not matched. An amplifier control 51 can then be used to tune the tuneable voltage controlled amplifier 48 to eliminate the global noise on the output of the differential amplifier 45 thereby matching the outputs from the two coils appropriately.

In particular embodiments in this arrangement, a known global field of 1 kHz or so is applied to both coils, so as to achieve the appropriate coil matching for the gradient subtraction, but also a filter to remove 50 or 60 Hz (and harmonics) noise is applied to the output signal.

Figure 5:
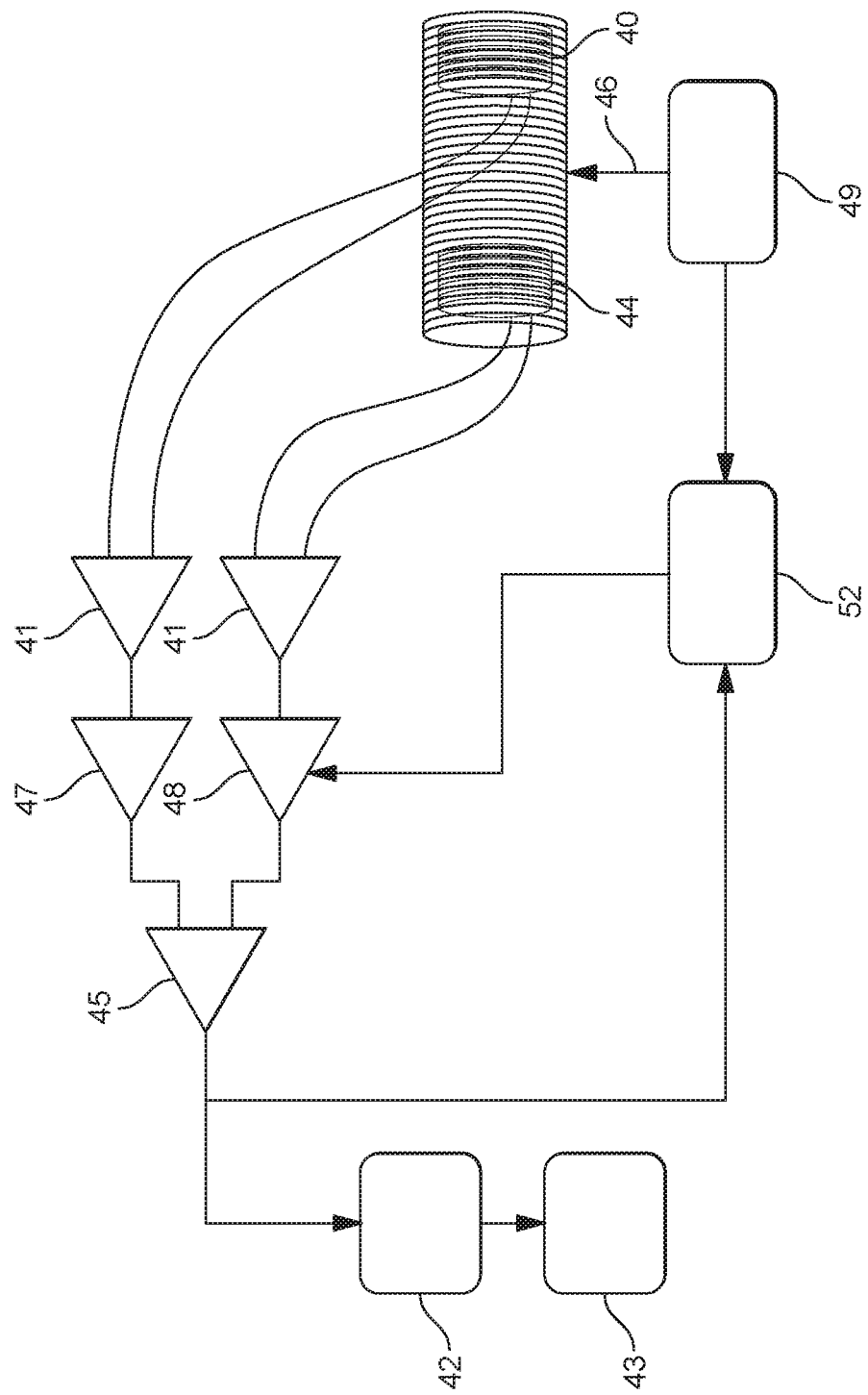

FIG. 5 shows a further variation on the FIG. 4 arrangement, but in this case using active coil matching. Thus, in this arrangement, the outputs of the coils 40, 44 are again channelled to appropriate detection circuits 41, and then to respective amplifiers 47, 48, at least one of which is tuneable. However, the tuneable amplifier 48 is tuned in this arrangement to remove the common mode noise using a lock in amplifier 52 or similar voltage controller that is appropriately coupled to the output from the differential amplifier 45 and the signal generator 49.

The above embodiments of the technology described herein show arrangements in which there is a single pickup coil that may be used to detect the magnetic field of the subject's heart. In these arrangements, in order then to make a diagnostic scan of the magnetic fields generated by a subject's heart, the single pickup coil can be moved appropriately over the subject's chest to take readings at appropriate spatial positions over the subject's chest. The readings can then be collected and used to compile appropriate magnetic field scans of the subject's heart.

It would also be possible to arrange a plurality of coil and detection circuit arrangements, e.g. of the form shown in FIG. 1, in an array, and to then use such an array to take measurements of the magnetic field generated by a subject's heart. In this case, the array of coils could be used to take readings from plural positions over a subject's chest simultaneously, thereby, e.g., avoiding or reducing the need to take readings using the same coil at different positions over the subject's chest.

Figure 6A:
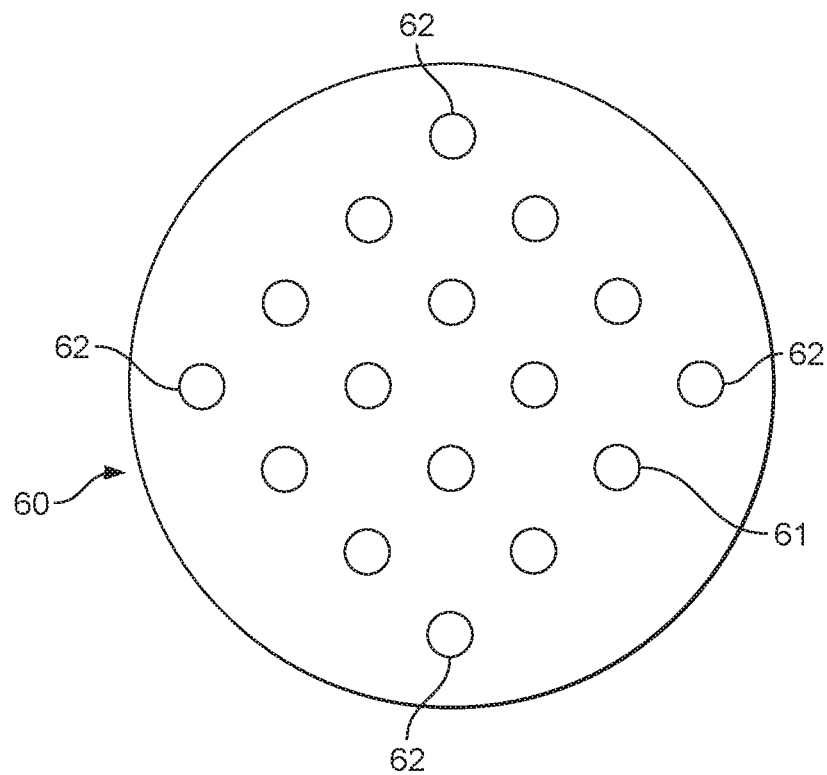
FIG. 6A shows schematically a coil arrangement in accordance with an embodiment of the technology described herein.
Figure 6B:
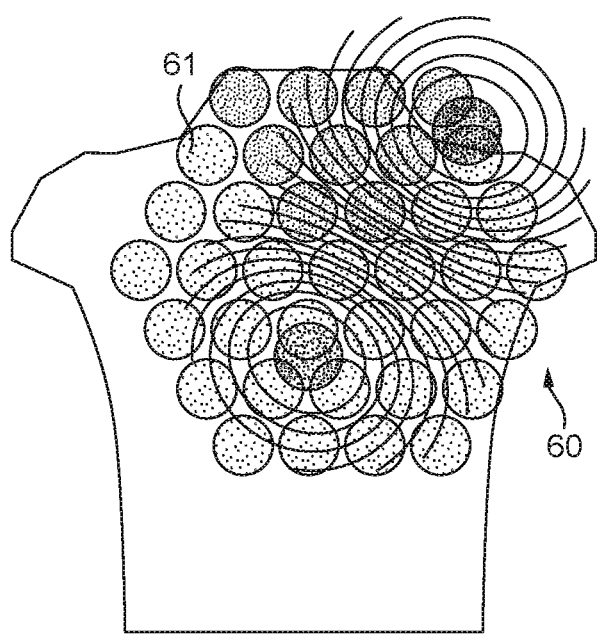
FIG. 6B shows schematically another coil arrangement in accordance with an embodiment of the technology described herein.

FIGS. 6A and 6B show suitable coil array arrangements that have an array 60 of 16 detection coils 61, which may be then placed over a subject's chest to measure the magnetic field of a subject's heart at 16 sampling positions over the subject's chest. FIG. 6A shows a regular rectangular array and FIG. 6B shows a regular hexagonal array. In these cases, each coil 61 of the array 60 should be configured as described above and connected to its own respective detection circuit (i.e. each individual coil 61 will be arranged and have a detection circuit connected to it as shown in FIG. 1).

The output signals from the respective coils 61 can then be combined and used appropriately to generate a magnetic scan of the subject's heart.

Other array arrangements could be used, if desired, such as circular arrays, irregular arrays, etc.

More (or less) coils could be provided in the array, e.g. up to 50 coils, or more than 50 coils. For example, where it is desired to measure the magnetic field of a different region of a subject's body (i.e. other than the heart), then an increased number of coils may be provided so as to provide an appropriate number of sampling points and an appropriate spatial coverage for the region of the subject's body in question.

It would also be possible in this arrangement to use some of the coils 61 to detect the background magnetic field for the purposes of background noise subtraction, rather than for detecting the wanted field of the subject's heart. For example, the outer coils 62 of the array could be used as background field detectors, with the signals detected by those coils then being subtracted appropriately from the signals detected by the remaining coils of the array. Other arrangements for background noise subtraction would, of course, be possible.

It would also be possible to have multiple layers of arrays of the form shown in FIG. 6, if desired. In this case, there could, for example, be two such arrays, one on top of each other, with the array that is closer to the subject's chest being used to detect the magnetic field generated by the subject's heart, and the array that is further away being used for the purposes of background noise detection.

To measure the magnetic fields generated by the heart, the above arrangements can be used to compile magnetic field scans of a subject's heart by collecting magnetic field measurements at intervals over the subject's chest. False colour images, for example, can then be compiled for any section of the heartbeat, and the scans then used, for example by comparison with known reference images, to diagnose various cardiac conditions. Moreover this can be done for significantly lower costs both in terms of installation and on-going running costs, than existing cardiac magnetometry devices.

Figure 7:
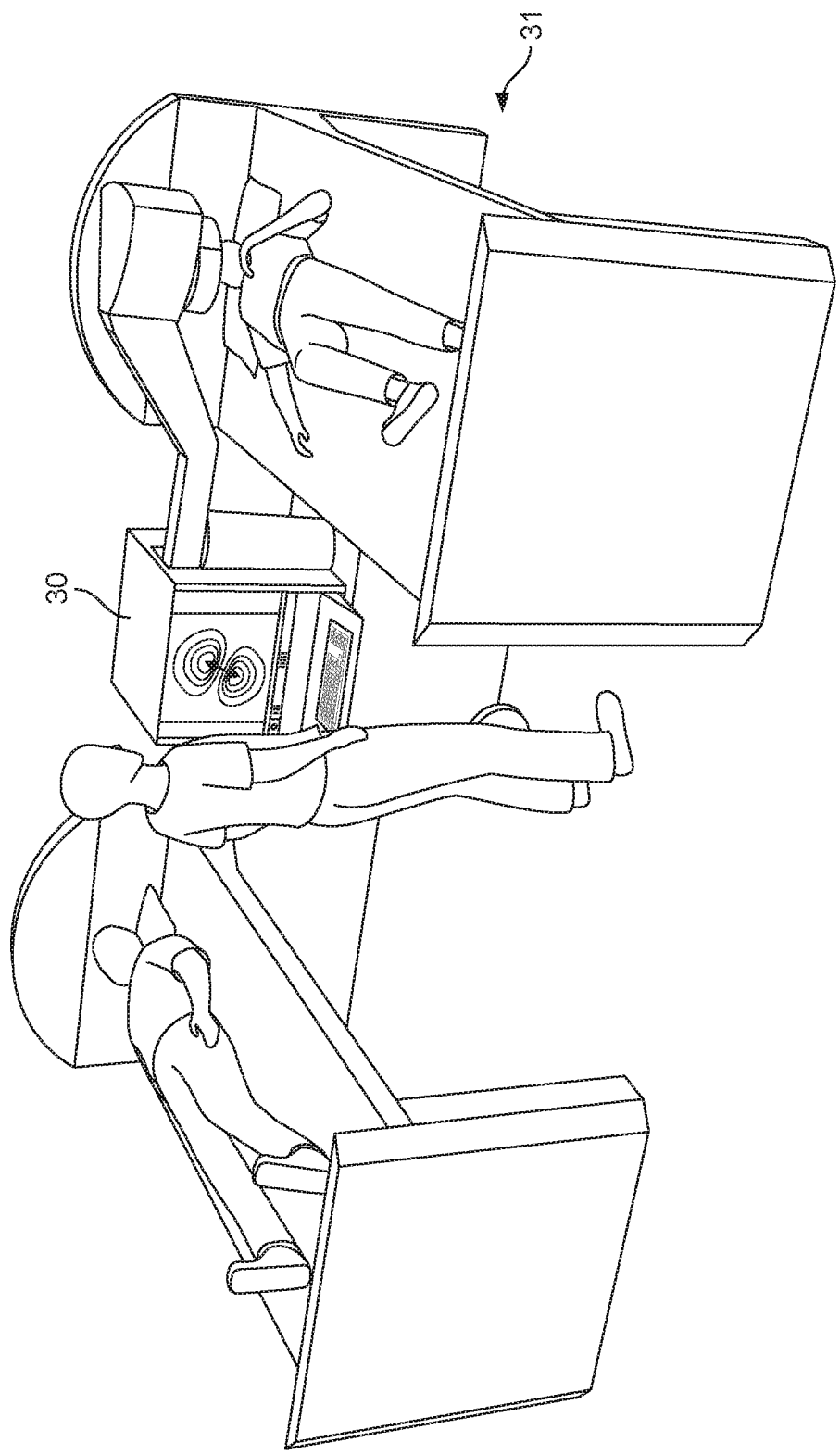
FIG. 7 shows a further exemplary arrangement of the use of an embodiment of the technology described herein when detecting the magnetic field of a subject's heart.

FIG. 7 shows an exemplary arrangement of the magnetometer as it is envisaged it may be used in a hospital, for example. The magnetometer 30 is a portable device that may be wheeled to a patient's bedside 31 where it is then used to take a scan of the patient's heart (e.g.). There is no need for any magnetic shielding, cryogenic cooling, etc. The magnetometer 30 can be used in the normal ward environment. (Magnetic shielding and/or cooling could, however, be provided if desired.)

In the technology described herein, each coil's 61 length, l, its outer diameter, D, and its inner diameter, $D_i$, are carefully selected in order to improve the coil's 61 sensitivity to bio-magnetic fields.

In its simplest form, an induction coil is an electronic component that responds to changes in a magnetic field by producing an electromotive force (EMF, or voltage difference) in opposition (due to Lenz's law) to the field that produced this force. From this induced potential difference (voltage), a current will flow through the coil.

It has been shown mathematically that the maximum possible inductance of a coil with an air core for a given length of wire is the Brooks coil.

Figure 8:
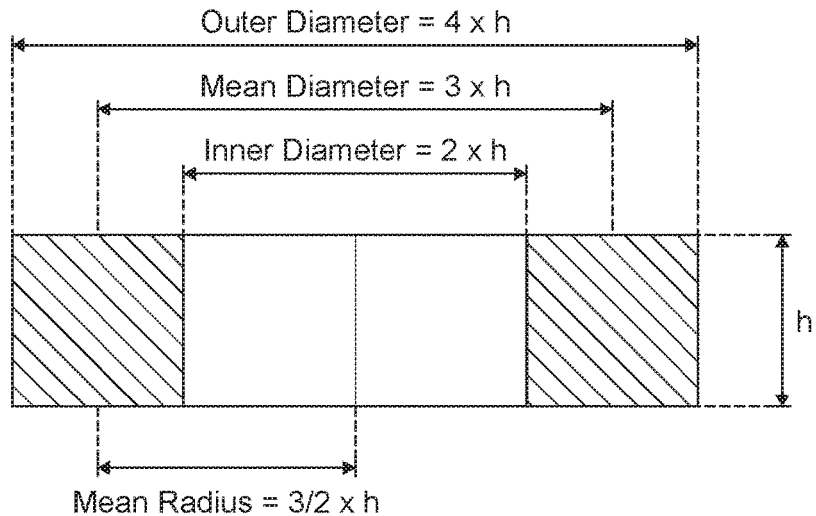
FIG. 8 shows schematically the coil configuration for a Brooks coil.

FIG. 8 illustrates the design of the conventional Brooks coil. Here the winding cross-section is square and the overall diameter of the coil has a width of 4 times one of the sides of the square. The inductance L for the Brooks coils is given by the equation:

$$L \approx 0.02591 h N^2 \mu_0 H$$

where h is the height or length of one side of the square winding cross section, N is the total number of turns, $\mu_0$ is the permeability of free space, and H is the magnetic field strength. This can also be expressed in terms of the mean winding radius ($r_{mean}$) of the coil as follows:

$$L \approx 0.016994 r_{mean} N^2 \mu_0 H$$

H can also be expressed as BA which represents the magnetic flux density B multiplied by the cross-sectional area A of the coil:

$$H = BA = B\pi r_{mean}^2$$

It can be seen from these equations that to increase the inductance L of an air-core coil, either the radius of the coil $r_{mean}$ or the number of turns N must be increased. However, both of these add to the electrical resistance of the coil.

Figure 9:
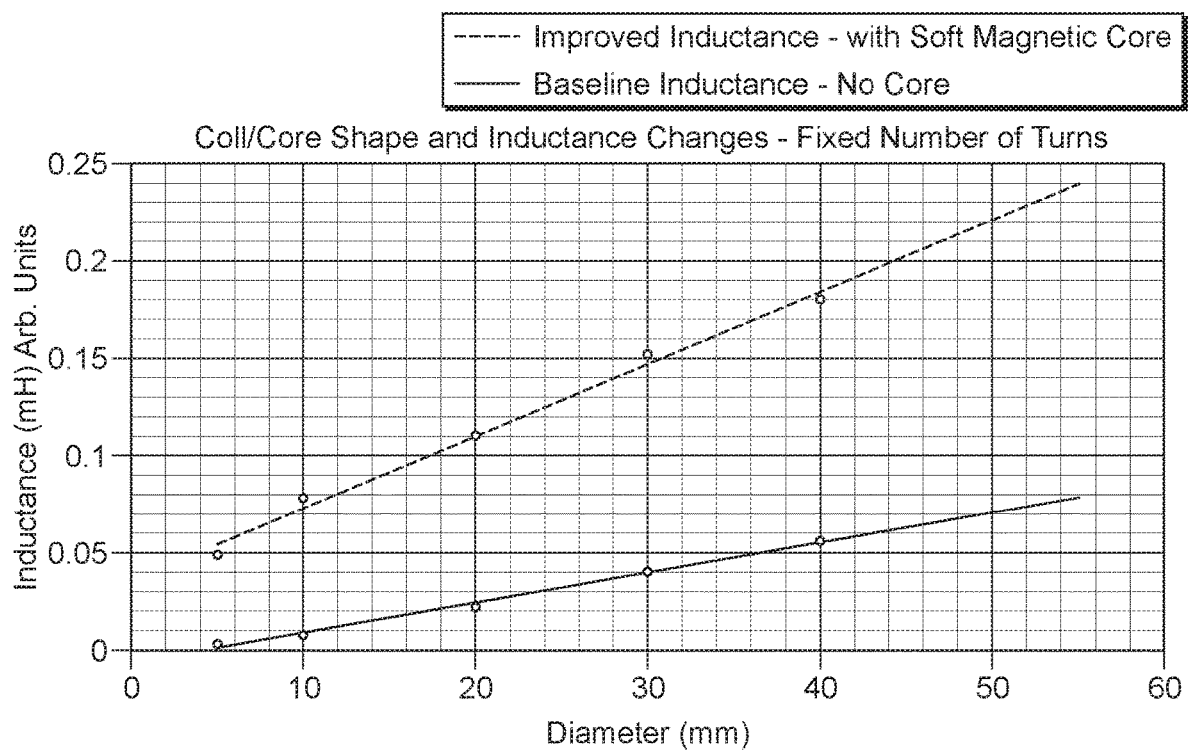
FIG. 9 illustrates the effect of a coil's outer diameter on the coil's inductance.

FIG. 9 illustrates the effect of a coil's outer diameter, D, on the coil's inductance, L. In FIG. 9, the solid (lower) line shows the change in measured inductance L with diameter D of a coil that does not have a magnetic core, while the dashed (upper) line shows the change in measured inductance L with diameter D of a coil that has a soft magnetic core. Each coil measured in FIG. 9 had a fixed number of (30) turns. FIG. 9 shows that the presence of a soft magnetic core improves the inductance of the coil. Moreover, FIG. 9 shows that, for a fixed number of turns, the inductance L of a (single-layer) coil increases with its diameter (and cross-sectional area), allowing it to cut more magnetic flux lines.

Most conventional coil designs are based upon the Brooks coil and winding cross-sections. Air core coils are commonly used because they do not saturate easily and experience low losses, particularly at higher frequencies. Often air-gaps are deliberately introduced to certain inductors to reduce core saturation. Inner-to-outer diameter ratios are typically small. Large gauges of wire are chosen to reduce resistance/noise which results in physically large and heavy coils.

Another way to increase the sensitivity of an induction coil without increasing resistance is to introduce a soft-magnetic (ferrous) material (core) into the centre of the coil.

Ferrous cores are materials possessing high magnetic permeability and can be used to guide and confine magnetic fields. When introduced to an induction coil, they can greatly enhance the magnetic field strength. Ferrous cores act as flux concentrators within the coil which draw magnetic field lines to themselves, greatly increasing the inductance of the coil.

The inductance of a single-layer coil with a ferrous core is given by the following formula:

$$L = \mu_e \mu_0 N^2 BA$$

Here, $\mu_e$ refers to the effective permeability of the ferrous material in the centre (which is equal to 1 in the case of air).

FIG. 9 shows the increase in inductance for each coil with the introduction of a soft magnetic material core. It can be seen that a 10 mm diameter coil with a core has an equivalent induction to a 50 mm diameter coil without a core despite having 25× less cross-sectional area (and significantly, lower resistance).

However magnetic cores are not without their downsides as they can introduce losses primarily through hysteresis and eddy currents. High permeability alone is not a sufficient for a material to be selected as a magnetic core. Generally speaking materials with low coercivity are preferred as it allows them to respond to changing (AC) fields with lower losses (materials with high coercivity can be considered permanent magnets).

A number of coils that use a magnetic core and that are configured in accordance with embodiments will now be discussed.

Increasing the inductance of a coil has a number of positive effects, including increasing the coil's sensitivity to magnetic fields, and increasing the time constant of the voltage rise time, thereby shifting the frequency response of the coil to lower frequencies (which are more typical of biological signals) and acting as a choke for higher-frequency sources of noise.

According to various embodiments, amorphous metallic alloys (sometimes referred to as metallic glasses or glassy metals) cores are used, e.g. in place of conventional pressed iron powder cores. These materials differ from traditional metallic materials and alloys in that they have highly disordered atomic structures instead of conventional crystalline or poly-crystalline lattices, and as such have a number or unique properties.

By alloying with certain magnetic materials such as iron, cobalt, and nickel, very high magnetic permeability and susceptibility materials are possible, such as Metglas 2714a or FINEMET. Their high resistance reduces eddy current losses when subjected to alternating magnetic fields; their low coercivity also reduces losses.

As such, a core of, for example, Metglas 2714a, nanocrystalline materials (i.e. polycrystalline materials with very small grain sizes, the space between which are filled with amorphous material), or MuMetal, may be used.

The Applicants have recognised that the effective permeability ($\mu_e$) of the magnetic core will depend both of the relative permeability ($\mu_r$) of the magnetic material, and also on the geometry of the core. In particular, the effective permeability ($\mu_e$) depends on the core's geometry-dependent demagnetizing factor $N_{demag}$:

$$\mu_e = \frac{\mu_r}{1 + N_{demag} \cdot (\mu_r - 1)}, \text{ where:}$$

$$N_{demag} \cong \frac{D_C^2}{l_C^2} \cdot \left( \ln \frac{2l_C}{D_C} - 1 \right).$$

Here, $D_c$ and $l_c$ are the diameter and length of the core.

For sufficiently large relative permeabilities, the effective core permeability is almost independent of material properties because this formula simplifies to:

$$\mu_e \approx \frac{1}{N_{demag}}$$

Figure 10:
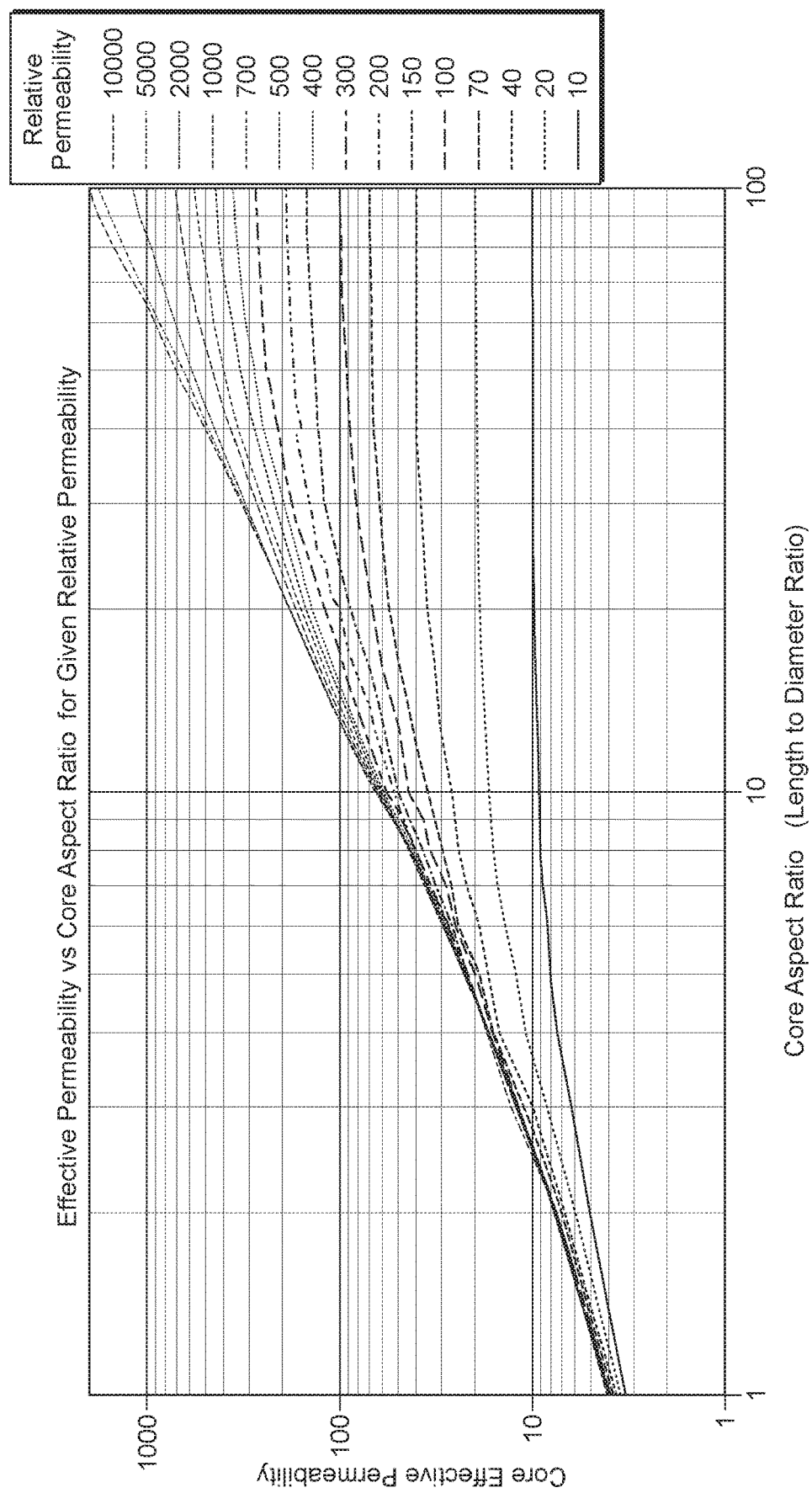
FIG. 10 illustrates the effect of a core's aspect ratio on its effective permeability.

FIG. 10 illustrates the effect of a core's aspect ratio on its effective permeability, $\mu_e$. As can be seen from FIG. 10, a material with a relative permeability of 10,000 may have an effective permeability of 4 when the length and diameter of the core are equal, or an effective permeability of >1000 when the core is 100 times longer than it is wide.

Figure 11:
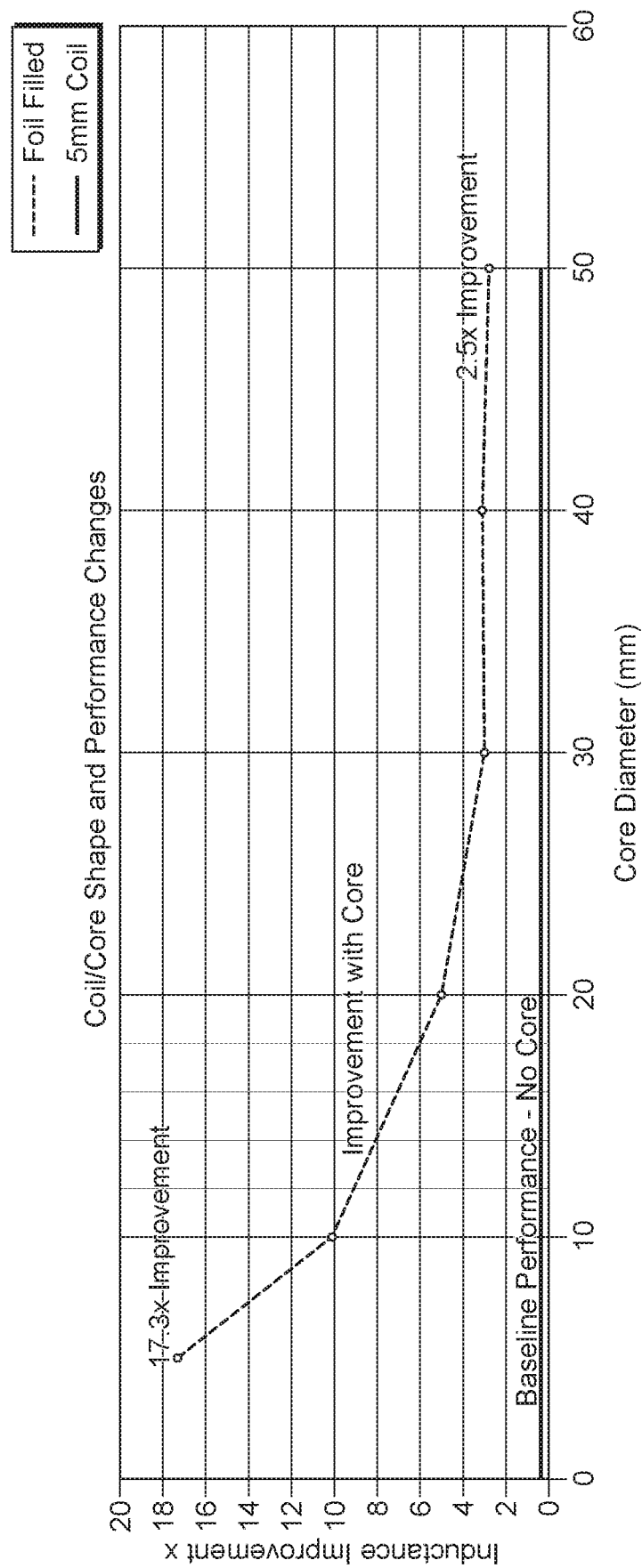
FIG. 11 illustrates the effect of a core's aspect ratio on its effective permeability.

This can be seen more readily by re-plotting the data from air-core coils (depicted in FIG. 9) and scaling the inductance to be relative to that of the coil without a core present. This is shown in FIG. 11. Here, with the addition of a fixed core length (50.8 mm), but variable core diameter (x-axis), drastically different values of inductance are seen for the same electrical resistance coil. Coils with a core diameter of 5 mm (10:1 aspect ratio) exhibit a ~17 times increase in measured inductance compared to only a ~2.5 times increase for coils with a 50 mm diameter core (~1:1 aspect ratio).

Taking this insight to its logical extreme, the most sensitive coils have a high permeability core, many turns, present a large cross-sectional area and maintain a high aspect ratio. Unfortunately physical constraints mean that it is not practical to produce a coil larger than a certain length and so a compromise must be struck.

In this regard, the outer diameter of the coil, D, should be limited to around 10 cm or less, in order to provide a coil having an overall size that can achieve a spatial resolution that is suitable for medical magnetometry (and in particular for magneto cardiography).

The ratio of the coil's length to its outer diameter should be relatively large (i.e. 0.9 or more), so that the coil is relatively long (along its axis) for its width. This means that the coil can comprise a magnetic core that has a relatively large length to diameter ratio, $l_c:D_c$, (and accordingly a high effective permeability, $\mu_e$), and accordingly that the coil will have a relatively high inductance, L.

However, the magnetic field strength falls off proportionally with $1/r^3$, so turns that are twice as far away from the source of the magnetic field experience a field strength reduced by a factor of 8. Thus, for example, turns 10 cm from the magnetic field source (e.g. the top of heart, or middle, etc.) will experience a magnetic field strength of 12.5% of the strength experienced at 5 cm from the source; turns 15 cm from the source will experience a magnetic field strength of 3.7% the strength experienced at 5 cm, and 29% of the strength experienced at 10 cm; and turns 20 cm from the source will experience a magnetic field strength of 1.56% of the strength experienced at 5 cm, 12.5% of the strength experienced at 10 cm, and 42% of the strength experienced at 15 cm.

This means that turns at the top and bottom of coil experience very different field strengths. This in turn means that there is no benefit in designing a very long coil despite improvements due to the aspect ratio. From these considerations, it was determined that the optimum coil length, l, is ~50 mm. Beyond this length, the field of the heart weakens and diverges significantly, and the magnetometer device becomes less practical and unwieldy.

Furthermore, the Applicants have recognised that the ratio of the coil's inner diameter to its outer diameter (i.e. the ratio of the inner diameter of the winding(s) to the outer diameter of the winding(s)), $D_i:D$, should be relatively large, i.e. 0.6 or more. This means that the coil's winding(s) are packed relatively tightly in the direction orthogonal to the core's axis (i.e. have a relatively narrow spread of radial distances from the coil's axis in the direction orthogonal to the coil's axis). This in turns means that the turns of each layer of the coil will be relatively close to the core.

In addition, arranging the outer surface of the core to be in contact with the coil winding(s), means that the winding(s) are as close as possible to the core. Turns of the coil in direct contact or in close proximity with the core receive a large boost to their measured inductance values, but the effect can be almost negligible for the outer turns.

On the other hand, each coil should comprise plural layers of turns, since increasing the number of layers of turns has the effect of increasing the coil's inductance (e.g. without increasing the coil's length, l). However, increasing the number of layers of turns will decrease the ratio of the coil's inner diameter to its outer diameter, $D_i:D$.

Figure 12:
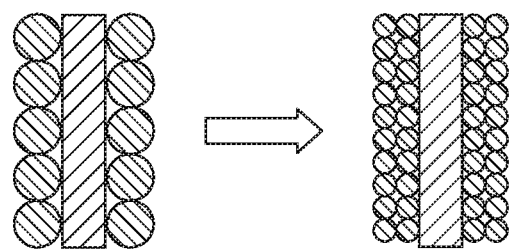
FIG. 12 shows schematically a single layer coil and a multi-layer coil.

This can be addressed to some degree by using a wire with a smaller gauge and hence cross-sectional area, and so more turns (and thus increased wire length) can be added in the same volume, or an identical number of turns can be placed in close proximity to the core. This is illustrated by FIG. 12.

This change comes at the expense of increased resistance as it is proportional to cross-sectional area (A):

$$R = \frac{\rho l}{A}$$

However, if the resistance becomes too high, then the Johnson-Nyquist noise can becomes a problem (this can increase the number of cycle averages needed and prolong scan times, or increase the size of the smallest detectable feature), and the amplification electronics need to be suitably modified to ensure sufficient current flow. Though the temperature can be reduced to minimize noise levels, cryogenic refrigerants (such as liquid nitrogen or helium) are not practical, e.g. in terms of cost and safe containment.

Figure 13A:
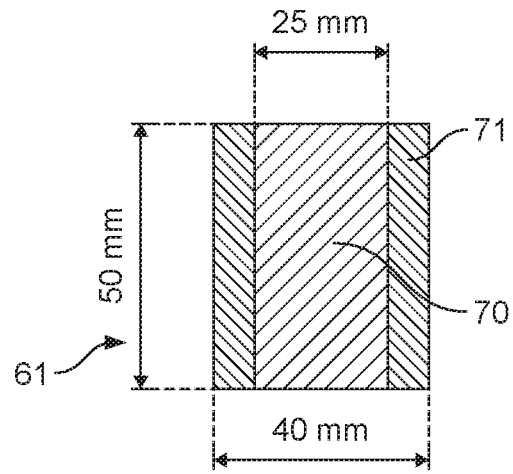
FIG. 13A shows schematically a coil in accordance with an embodiment of the technology described herein.
Figure 13B:
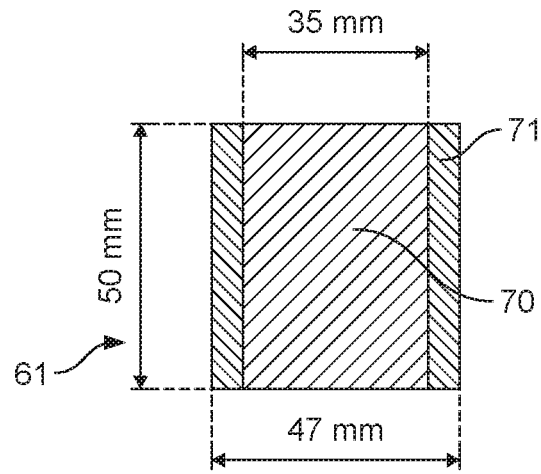
FIG. 13B shows schematically another coil in accordance with another embodiment of the technology described herein.

The above factors must be carefully balanced when designing coils for use in medical magnetometry. In this regard, the Applicants have found that a particularly balance between the above described competing factors can be found by providing a coil or coils with the following configuration:

$$D \approx 4.7 \text{ cm};$$
$$l \approx 5 \text{ cm; and}$$
$$\frac{Di}{D} \approx 0.745$$

where D is the outer diameter of the coil, l is length of the coil, and $D_i$ is the inner diameter of the coil. This arrangement is depicted in FIG. 13B. Coils having these proportions have been found to have a relatively high inductance, L.

In various other particular embodiments, the or each coil has the following configuration:

$$D \approx 4 \text{ cm};$$
$$l \approx 5 \text{ cm; and}$$
$$\frac{Di}{D} \approx 0.625$$

where D is the outer diameter of the coil, l is length of the coil, and $D_i$ is the inner diameter of the coil. This arrangement is depicted in FIG. 13A. Coils having these proportions have been found to have an even higher inductance, L.

The Applicants have also found that it is not necessary to have a completely solid core, so long as the overall dimensions of the core are maintained. Indeed, a thin strip or ribbon (e.g. <35 μm thick) of Metglas 2714a foil rolled into a hollow cylinder (or e.g. a laminated stack of layers formed into a hollow cylinder) and placed into a coil can yield a similar (or even greater) increase in coil inductance to a ferrite rod of the same overall dimensions because of its high relative permeability ($\mu_r$). This results in significant reductions in both material costs and coil weight. Similar benefits can be obtained using plural laminated layers of foil.

The Applicants have also found that, for these high aspect ratio core shapes, it is important to place the core material in direct contact with (or close to) the windings. This minimizes the potential for leakage inductance and partially serves as a choke to filter out undesired high-frequency noise. As such, the coils may comprise self-supporting bonded coils (i.e. instead of winding onto a bobbin and introducing an "air" gap between core and wire).

The wire used is 0.25 mm copper or copper clad aluminium. By reducing the wire gauge and increasing the length of the coil, many more turns are able to be wound, significantly increasing the inductance of the coil. By using copper clad aluminium, the weight of the coil is significantly reduced (e.g. compared to copper). If the weight of the coil grows too large, then the cost and engineering challenge of safely fixing them above the patient increases. Copper clad aluminium can offer significant (>50%) weight reductions at the price of increased resistance.

The coils according to various embodiments are around 10 times more resistive, so exhibit around 3 times more thermal noise than the coils described in WO2014/006387. The inductance however is around 11 times higher, so the signal to noise ratio is improved by a factor of more than 3.

Figure 14:
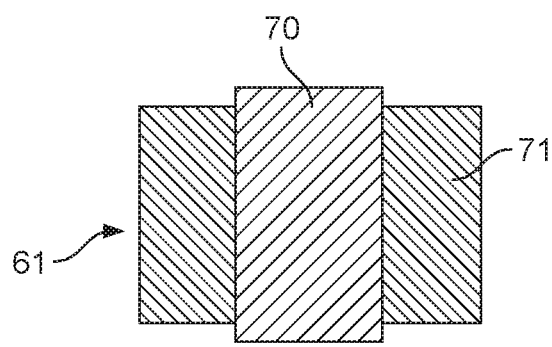
FIG. 14 shows schematically a coil in accordance with an embodiment of the technology described herein.

Although as shown in FIG. 13, the coil's 61 core 70 may have the same length as the winding 71, as illustrated by in FIG. 14, it would also be possible for the core 70 to be longer than the length of the winding 71. This can increase the aspect ratio of the core 70, and so increase its effective permeability. (It should be noted that FIG. 14 is for illustrative purposes only, and is not to scale.)

The presence of a magnetic core significantly increases the inductance of the coils. The use of air cored coils having the configuration described herein to detect biological magnetic fields of interest would necessitate significantly increased scan times in order to obtain the same signal to noise ratio.

It can be seen from the above that the technology described herein, in its embodiments at least, provides a magnetic imaging device that can be deployed effectively from both a medical and cost perspective in a wide range of clinical environments, e.g. for use when detecting magnetic fields generated by the heart. The magnetometer is, in particular, advantageous in terms of its cost, its practicality for use in clinical environments, and its ability to be rapidly deployed for near patient diagnosis and for a wide range of applications. It is non-contact, works through clothing, fast, compact and portable and affordable. An image can be recovered with high resolution after a minute of signal recording and absolute "single beat" sensitivity is potentially possible. With appropriate data treatment, slight patient motion will not significantly degrade the image.

This is achieved, in embodiments of the technology described herein at least, by using an improved design of detection coil that has a particular configuration and that is configured to detect the time varying magnetic of the (e.g.) heart.

The invention claimed is:
1. A magnetometer system for medical use, comprising:
one or more induction coils for detecting a time varying magnetic field, each induction coil of the one or more induction coils having:
a maximum outer diameter of 10 cm or less;
a configuration such that a ratio of its length to its outer diameter is in a range 0.9 to 3, and a ratio of its inner diameter to its outer diameter is in a range 0.6 to 1; and
a magnetic core;

the magnetometer system further comprising a detection circuit coupled to each induction coil of the one or more induction coils and configured to convert a current or voltage generated in each induction coil of the one or more induction coils by the time varying magnetic field to an output signal for use to analyse the time varying magnetic field.

2. The magnetometer system of claim 1, wherein the one or more induction coils comprise plural induction coils arranged in one or more two or three dimensional arrays.

3. The magnetometer system of claim 1, wherein each induction coil of the one or more induction coils comprises plural layers of turns.

4. The magnetometer system of claim 1, wherein each induction coil of the one or more induction coils has a winding length of 10 cm or less.

5. The magnetometer system of claim 1, wherein each induction coil of the one or more induction coils has a configuration such that the ratio of its length to its outer diameter is in the range 1 to 1.5.

6. The magnetometer system of claim 1, wherein each induction coil of the one or more induction coils comprises wire having a radius less than 0.2 mm.

7. The magnetometer system of claim 1, wherein each magnetic core comprises a material with a relative permeability, $\mu_r$, of at least 1000.

8. The magnetometer system of claim 1, wherein each magnetic core comprises a magnetic amorphous metal alloy, a nano-crystalline material, a nickel-iron alloy or a cobalt-iron alloy.

9. The magnetometer system of claim 1, wherein for each coil of the one or more induction coils, the ratio of the coil's magnetic core's outer diameter to the coil's inner diameter, $D_c:D_i$, is 0.8 or more.

10. The magnetometer system of claim 9, wherein for each coil of the one or more induction coils, the ratio of the coil's magnetic core's outer diameter to the coil's inner diameter, $D_c:D_i$, is 0.9 or more.

11. The magnetometer system of claim 1, wherein the ratio of each magnetic core's length to its outer diameter, $l_c:D_c$, is at least 1.

12. The magnetometer system of claim 1, wherein each magnetic core is hollow.

13. A cardiac magnetometer system for analysing the magnetic field of a region of a subject's body, comprising the magnetometer system of claim 1.

14. The use of the magnetometer system of claim 1 for analysing the time varying magnetic field generated by a region of a subject's body.

15. A coil for use to detect a time varying magnetic field of a region of a subject's body, the coil comprising:
    an induction coil having a maximum outer diameter of 10 cm or less, and a configuration such that a ratio of the induction coil's length to its outer diameter is in a range 0.9 to 3, and a ratio of the induction coil's inner diameter to its outer diameter is 0.6 to 1; and
    a magnetic core.

16. A method of analysing a magnetic field of a region of a subject's body, the method comprising:
    using one or more induction coils to detect a time varying magnetic field of a region of the subject's body, each induction coil of the one or more induction coils having:
    a maximum outer diameter of 10 cm or less, and a configuration such that a ratio of its length to its outer diameter is in a range 0.9 to 3, and a ratio of the its inner diameter to its outer diameter is in a range 0.6 to 1; and
    a magnetic core;
    the method further comprising converting a current or voltage generated in each induction coil of the one or more induction coils by the time varying magnetic field of the region of the subject's body to an output signal; and
    using the output signal or signals from the one or more induction coils to analyse the time varying magnetic field generated by the region of the subject's body.

17. The method of claim 16, comprising using the one or more induction coils to detect the time varying magnetic field of the region of the subject's body in a non-magnetically shielded environment.

18. The method of claim 16, wherein the region of the subject's body comprises one of: the abdomen, bladder, heart, head, brain, chest, womb, one or more foetuses, or a muscle.

19. A method of analysing the magnetic field of a subject's heart, the method comprising:
    using the method of claim 16 to analyse the time varying magnetic field of the subject's heart.

* * * * *

UNITED STATES PATENT AND TRADEMARK OFFICE
CERTIFICATE OF CORRECTION

PATENT NO. : 11,547,337 B2
APPLICATION NO. : 16/492150
DATED : January 10, 2023
INVENTOR(S) : Grant et al.

Page 1 of 1

It is certified that error appears in the above-identified patent and that said Letters Patent is hereby corrected as shown below:

On the Title Page

Item (22) please replace "Nov. 11, 2018" with -- Nov. 29, 2018 --

In the Claims

Column 26, Line 21 (Claim 16, Line 9) please replace "the its inner" with -- its inner --

Signed and Sealed this
Twenty-third Day of May, 2023

Katherine Kelly Vidal
*Director of the United States Patent and Trademark Office*